US010064625B2

(12) United States Patent
Kahana et al.

(10) Patent No.: US 10,064,625 B2
(45) Date of Patent: Sep. 4, 2018

(54) CONNECTOR

(71) Applicant: MEDICAL CONNECTION TECHNOLOGY— MEDICONNTECH-M.C.T LTD, Kibbutz Beit Zera (IL)

(72) Inventors: Shay Kahana, Kibbutz Bet Zera (IL); Zvi Nitzan, Moshav Zofit (IL)

(73) Assignee: MEDICAL CONNECTION TECHNOLOGY— MEDICONNTECH—M.C.T. LTD, Kibbutz Bet Zera (IL)

( * ) Notice: Subject to any disclaimer, the term of this patent is extended or adjusted under 35 U.S.C. 154(b) by 347 days.

(21) Appl. No.: 14/759,235

(22) PCT Filed: Jan. 6, 2014

(86) PCT No.: PCT/IL2014/050012
§ 371 (c)(1),
(2) Date: Jul. 6, 2015

(87) PCT Pub. No.: WO2014/106850
PCT Pub. Date: Jul. 10, 2014

(65) Prior Publication Data
US 2015/0351768 A1 Dec. 10, 2015

Related U.S. Application Data

(60) Provisional application No. 61/749,331, filed on Jan. 6, 2013.

(51) Int. Cl.
*A61B 17/11* (2006.01)
*A61F 2/06* (2013.01)

(52) U.S. Cl.
CPC .............. *A61B 17/11* (2013.01); *A61F 2/064* (2013.01); *A61B 2017/1107* (2013.01); *A61B 2017/1132* (2013.01); *A61B 2017/1135* (2013.01)

(58) Field of Classification Search
CPC ............ A61B 17/0401; A61B 17/0485; A61B 17/06166; A61B 2017/06185; A61B 2017/0619; A61B 2019/444
See application file for complete search history.

(56) References Cited

U.S. PATENT DOCUMENTS 869,686 A * 10/1907 Buano .................... A63H 33/00
128/880
4,470,415 A * 9/1984 Wozniak ................ A61B 17/11
29/447

(Continued)

FOREIGN PATENT DOCUMENTS

EP 1055401 11/2000
JP 10309313 11/1998

(Continued)

*Primary Examiner* — Julie A Szpira
(74) *Attorney, Agent, or Firm* — Mark M. Friedman

(57) ABSTRACT

The present invention provides a device for connecting at least one biological structure, the device including a tubular member, a first opening at one end of the member, a second opening at a second opposing end of the member and a central cavity within the member for accommodating the at least one biological structure. The member includes a plurality of interwoven lengths configured for reversible radial enlargement of the member when the extremities are pushed inwards and reversible radial contraction of the member when the extremities are pulled outwards. The present invention further provides methods of connecting one or more biological structures.

21 Claims, 17 Drawing Sheets

(56) References Cited

U.S. PATENT DOCUMENTS

| | | | |
|---|---|---|---|
| 5,116,358 A * | 5/1992 | Granger | A61B 17/06004 606/224 |
| 5,139,505 A * | 8/1992 | Palmieri | A61B 17/11 606/153 |
| 5,254,127 A | 10/1993 | Wholey et al. | |
| 6,203,572 B1 * | 3/2001 | Johnson | A61F 2/08 606/108 |
| 7,279,008 B2 * | 10/2007 | Brown | A61B 17/0401 623/13.13 |
| 8,517,073 B2 * | 8/2013 | Bogart | A61B 17/0487 156/499 |
| 8,734,503 B2 * | 5/2014 | Orion | A61F 2/064 623/1.15 |
| 2002/0087176 A1 * | 7/2002 | Greenhalgh | A61F 2/064 606/155 |
| 2003/0065360 A1 | 4/2003 | Jacobs et al. | |
| 2006/0106423 A1 * | 5/2006 | Weisel | A61B 17/0401 606/232 |
| 2007/0293932 A1 * | 12/2007 | Zilla | A61F 2/06 623/1.11 |
| 2009/0306776 A1 * | 12/2009 | Murray | A61B 17/0401 623/13.12 |
| 2010/0030256 A1 | 2/2010 | Dubrul et al. | |
| 2011/0288566 A1 * | 11/2011 | Kubiak | A61B 17/1146 606/151 |

FOREIGN PATENT DOCUMENTS

| | | |
|---|---|---|
| RU | 2465846 | 4/2010 |
| WO | 9603084 | 2/1996 |
| WO | 0027313 | 5/2000 |

* cited by examiner

CONNECTOR

This application claims priority to U.S. Patent Application Ser. No. 61/749,331 filed on Jan. 6, 2013 and incorporated herein by reference in its entirety.

FIELD OF THE INVENTION

The present invention relates to a connector and a method of use thereof. Moreover, the present invention is of a connector for joining body tissues.

BACKGROUND OF THE INVENTION

In many surgical procedures, it is necessary to join blood vessels end to end. The procedure of connecting blood conduits, such as vessels, prostheses or grafts, which are brought into communication with one another is known by the term vascular anastomosis. The main aim of performing a vascular anastomosis is to achieve maximal patency rates. An important factor to achieve that goal is to minimize damage to the vessel walls.

The most common device for holding body tissues together after injury or during surgery is surgical suture. Suturing is the joining of tissues with needle and thread so that the tissues bind together and heal. This method was first described in about 3000 BC. Suturing is a cheap technique and is a method of choice for joining body tissue, such as in vascular anastomosis, but the technique suffers from disadvantages. A main drawback is that suturing is slow, prolonging surgery. This results in more time the patient must be anaesthetized and less available time for other patients in the operating theatre. Suturing is also not ideal in small blood vessels. A further problem resulting from stitching is leaking from the gaps between each stitch and damage to the vascular wall.

Alternative methods or adjuvants to the use of sutures in wound closure include gluing with medical grade adhesives, stapling, clips, laser welding, rings and stents. These methods may be quicker than suturing, but are not ideal. Adhesives are difficult to use in anastomosis of small blood vessels, may take time to work, may not be strong enough to hold together certain biological structures for the needed time period and may cause toxicity, leakage and aneurysm formation. Staples suffer from the disadvantage that they need to be removed and may cause more stenosis than sutures. Stents may result in early occlusion. Laser welding is costly, necessitating specialized surgical skills and may have reduced strength in larger-sized vessels. Clips are problematic in long term joining of vessels of larger diameter where the pressure is too high. Rings cause rigidity and a non-compliant anastomosis.

It would therefore be desirable to have a device and method for joining body tissues, which would be quick to use, provide uniform connection and patency without the problem of narrowing the lumen. It would also be advantageous if the method was of low cost and did not require unusual experience or skill. The present invention provides such a device and method.

SUMMARY

The invention may have several aspects. One aspect is a device for connecting at least one biological structure. The at least one biological structure may be a biological tissue, a blood vessel, a ligament, an intestinal structure, a nerve or part thereof. The device may be for connecting at least one biological structure with at least one other structure, wherein the at least one other structure may be at least one biological structure and/or at least one non-biological structure. The biological structure may be any suitable tubular structure, which may be relatively cylindrical and hollow, which may be solid, which may have at least one cavity, which may be rounded and which may be relatively flat or a combination thereof. The biological structure may be a severed or cross-sectioned biological structure. The device may include an elongated tubular member, a first opening at one end of the member, which may be a distal end, a second opening at a second opposing end of the member, which may be a proximal end, and a central cavity within the elongated member for accommodating the at least one biological structure. The elongated member may include a plurality of interwoven lengths configured for reversible radial enlargement of the member when a pushing force is applied, such as when the extremities are pushed inwards and reversible radial contraction of the member when a pulling force is applied, such as when the extremities are pulled outwards.

In various embodiments, the device may be a tubular device. The device may be cylindrical. The device may be rounded or may have degrees of roundness. In some examples the device may be relatively square. The device may conform to the shape of the at least one biological structure. The interwoven lengths may be configured as a tubular braid. The plurality of interwoven lengths may be at least one of wires, filaments, sheets, ribbons, sheaths, threads, strips and tubes. The plurality of lengths may include a plurality of warps and a plurality of wefts, wherein the wefts are at an angle to the warps. The angle may be reduced by pulling the device outwards and the angle may be increased by pushing the device inwards. The device may include an external surface and an internal surface, a first section for accommodating a first biological structure or a first non-biological structure and a second section for accommodating a second biological structure or a second non-biological structure. A 'joining line' may refer to the line or point adjacent to or where the first section and the second section meet and/or where the first inserted structure and the second inserted structure contact each other. The device may be coated with at least one layer of coating. The at least one layer of coating may include a glue, and/or a therapeutic agent. The device may include a stop element for correct positioning at the joining line of the at least one biological structure and for preventing displacement of the at least one biological structure beyond the stop element. The device may include at least one unidirectional movement prevention element for preventing displacement of an inserted biological structure. The first section may feature a unidirectional movement promotion element for promoting movement in a direction through the first opening towards the joining line and preventing displacement away from the joining line towards the first opening and the second section may feature at least one unidirectional movement prevention element for promoting movement in a direction through the second opening towards the joining line and preventing displacement away from the joining line and towards the second opening. The unidirectional movement prevention element may include at least one spike. The at least one spike may be substantially parallel to the elongation direction of the device. The device may tighten about the at least one biological structure when at least one of the pushing force is eliminated, at least one of the extremities are pulled outwards, such as when a pulling force is applied, the at least one biological structure is displaced and the device is returned to or is in its relaxed state. The device may connect end to end a first part of a severed blood vessel with a second part of a severed blood vessel, or with at least one non-biological structure, wherein the non-biological structure may be a tube, a catheter, a synthetic graft, an inlet of a machine, an outlet of a machine, a wire and a combination thereof. The device may connect two structures, where each structure has different dimensions. The interwoven lengths at the extremities of the device may be folded into the braid or weave. The device may be fully disposable.

An additional aspect is a method of use of the device of the present invention. The method may be a method of connecting at least one biological structure. The method may include providing at least one device of the present invention. The method may feature inserting a first biological structure or part thereof into the cavity of the device through the first opening of one end of the tubular member and stopping insertion of the first biological structure at a stop element. The method may include inserting a second structure, wherein the second structure is at least one of, a biological structure which is not the same as the first biological structure, a second part of the first biological structure and a non-biological structure, into the cavity of the device through the second opening of the second end of the tubular member and stopping insertion of the second structure at a stop element, or on contact with the first biological structure, which may be at a joining line.

In various embodiments, the method may include the step of pulling at least one extremity of the tubular member to secure the device about the at least one biological structure. Inserting may feature pushing the at least one end of the member for reversible radial enlargement of the device, which may be before inserting the at least one biological structure. The method may include the step of gluing, which may include gluing the structures to be joined. The method may include preventing movement of the inserted at least one biological structure in an opposite direction to the direction of insertion of the at least one biological structure, with at least one unidirectional movement prevention element.

A further aspect is a method of production of a device of the present invention. The method may include providing a plurality of lengths of filaments and tubularly braiding the plurality of lengths of filaments to form a tubular braid. The method may include applying a plurality of at least one unidirectional movement prevention elements to the device, the applying which may be done before the braiding or after the braiding. The method may include applying at least one coating to the tubular braid. The coating may be applied to all the inner surface of the tubular braid or parts of the inner surface of the tubular braid. The at least one coating may include a glue. The method may include folding the extremities of the interwoven lengths into the braid.

Another aspect is a multipart device for connecting at least one biological structure. The multipart device may include a plurality of devices for connecting at least one biological structure with at least one structure. The plurality of devices may include at least one first device and at least one second device. Each of the plurality of devices may include an elongated tubular member, the elongated tubular member featuring a plurality of interwoven lengths, the plurality of interwoven lengths configured for reversible radial enlargement of the member when a pushing force is applied to at least one end of the member and reversible radial contraction when a pulling force is applied to at least one end of the member. Each of the plurality of devices may include a first opening at a distal end of the member, a second opening at a proximal end of the member and a central cavity within the elongated tubular member for accommodating the at least one biological structure. Each of the plurality of devices may include an attachment means at the proximal end of the member, wherein the attachment means of the first device corresponds with the attachment means of the second device for attachment of the proximal end of the first device with the proximal end of the second device to form a multi-part device for end to end attachment of an at least one biological structure accommodated in the cavity of the first device and at least one structure accommodated in the second device.

The multipart device may include a first connectable part for accommodating a biological structure or a non-biological structure and a second connectable part for accommodating a biological structure or a non-biological structure. The first part of the multipart device may include a tubular elongated member, a first distal end with a first opening through which the biological structure can be inserted and a second proximal end with a second opening. The second proximal end may feature one part of an attachment means. The elongated member may include a central cavity for accommodating the at least one biological structure and the elongated member may include a plurality of interwoven lengths configured for reversible radial enlargement of the member when the ends are pushed inwards and reversible radial contraction of the member when the ends are pulled outwards. The second part of the multipart device may include a tubular elongated member, a first distal end with a first opening through which the biological structure can be inserted and a second proximal end with a second opening. The second proximal end may feature a part of an attachment means corresponding to the attachment means of the proximal end of the first part of the multipart device. The elongated member may include a central cavity for accommodating the at least one biological structure, wherein the elongated member may feature a plurality of interwoven lengths configured for reversible radial enlargement of the member when the ends are pushed inwards and reversible radial contraction of the member when the ends are pulled outwards. The first part of the multipart device and the second part of the multipart device may attach to each other by attachment of the first part attachment means with the corresponding second part attachment means of the multipart device to form a multipart device for end to end attachment of the at least one biological structure accommodated in the cavity of the first part of the device and the at least one structure accommodated in the cavity of the second part of the multipart device. In some non-limiting examples, the first part attachment means and the second part attachment means may be configured for attachment to a clamp or clip or suitable holding means, which may be a standalone holding means and which may not be for attachment of the first part to the second part of the multipart device.

In various embodiments, each part of the multipart device may be a tubular device. The interwoven lengths may be configured as a tubular braid. The plurality of lengths may include a plurality of warps and a plurality of wefts, wherein the wefts are at an angle to the warps. The angle may be reduced by pulling each or either part of the device and the angle may be increased by pushing each or either part of the device inwards. Each part of the multipart device may include an external surface and an internal surface. The internal surface and/or the external surface may be coated with at least one layer of coating. The at least one layer of coating may include a glue, and/or a therapeutic agent. Each part of the multipart device may include at least one stop element. The internal surface of each part of the multipart device may include at least one unidirectional movement prevention element for preventing displacement of an inserted at least one biological structure away from the proximal end of the elongated member towards the distal end of the elongated member. The unidirectional movement prevention element may be a spike. The spike may be positioned substantially parallel to the elongation direction of the multipart device. The connected multipart device may connect end to end a first part of a severed blood vessel with a second part of a severed blood vessel, or with at least one non-biological structure, wherein the non-biological structure may be a tube, a catheter, a synthetic graft, an inlet of a machine, an outlet of a machine, a wire and a combination thereof. The multipart device may tighten about the at least one biological structure or other structure accommodated in the multipart device when at least one of a pushing force is eliminated, the ends of the device move apart, the at least one biological structure moves towards the distal end and the device enters a relaxed state.

A still further aspect is a method of using at least one multipart device for connecting at least one biological structure. The method may include providing at least one multipart device of the present invention. The multipart device may be provided in a disconnected state. The method may feature inserting a first biological structure or part thereof through the distal end of a first part, such as a first tubular member of the multipart device towards the proximal end of the first part of the multipart device and stopping insertion of the first biological structure when it reaches the proximal end. The proximal end may include a stop element. The method may feature inserting a second biological structure or a non-biological structure, wherein the second biological structure is a biological structure, which is not the same as the first biological structure, or is a second part of the first biological structure, through the distal end of a second part, such as a second tubular member of the multipart device towards the proximal end of the second part of the multipart device and stopping insertion of the second structure when it reaches the proximal end. The proximal end may include a stop element. The method may include attaching the first part of the multipart device to the second part of the multipart device by connecting an attachment means at the proximal end of the first part of the multipart device with the corresponding attachment means at the proximal end of the second part of the multipart device. The method may include the step of pulling at least one of the distal ends to secure at least one part of the device about the at least one inserted structure. Inserting may include pushing at least one of the distal ends for reversible radial enlargement before or simultaneously with inserting the at least one biological structure. The method may include the step of gluing, which may include gluing the ends of the inserted structures to be joined. The method may also include use of at least one unidirectional movement prevention element for preventing movement in an opposite direction to the direction of insertion of the inserted at least one biological structure and/or non-biological structure, such as configuring an internal surface of at least one of the tubular members with at least one unidirectional prevention movement element.

An aspect is a system such as a system for replacement of and/or augmentation of suturing in a bypass procedure of a blocked blood tissue. The system may include a blood vessel to bypass a blockage, the blood vessel comprising a first extremity and a second extremity. The system may include a first connectable part, such as a first tubular member and a second connectable part, such as a second tubular member of a multipart connector device, the first connectable part for connecting the first end of the bypass blood vessel to a first incision in a blocked blood vessel, such as an artery on a first side, such as before the blockage and the second connectable part for connecting the second end of the bypass blood vessel to a second incision in the blocked blood vessel, such as an artery on a second side of the blockage, such as after the blockage. The system may also include a plurality of clamping means, such as a clamp or clip, a first clamping means for disposing about the blocked blood vessel, such as an artery at the first incision and a second clamping means for disposing about the blocked blood vessel, such as an artery at the second incision. Each clamping means may be for attaching to and holding one respective part of the multipart device against an incision of the blocked blood vessel, such as an artery in a position for facilitating blood flow in the blocked blood vessel, such as an artery via the bypass blood vessel. The blood flow may be from the blocked blood vessel, such as an artery through the first incision into the bypass blood vessel and through the second incision into the blocked blood vessel, such as an artery.

A further aspect is a multi-tubular device including at least three devices, such as N≥3 featuring N≥3 elongated tubular members, which are interconnected. Each tubular elongated member may feature a plurality of interwoven lengths configured for reversible radial enlargement of the member when the ends are pushed inwards and reversible radial contraction of the member when the ends are pulled outwards. Each tubular elongated member may have a first distal end with a first opening through which at least one biological structure can be inserted and a central cavity within the elongated tubular member for accommodating the at least one biological structure. The first distal end is at an open extremity of the multi-tubular device. The multi-tubular device may include N openings corresponding to the openings at the distal ends of the N interconnected tubular members. Each tubular elongated member may include a second proximal end of the elongated member. The proximal ends of the N interconnected tubular members are connected to each other, such that the structures inserted through the distal openings of the tubular members into the cavities of the elongated members of the N interconnected devices can contact and connect to each other at an internal point of the multi-tubular device adjacent to the joined proximal ends of the N interconnected devices.

In various embodiments the multi-tubular device may be for joining at least one biological structure, wherein the at least one biological structure is at least one of a body tissue, a blood tissue, a blood vessel, a plurality of parts of a blood vessel, a plurality of blood vessels, a plurality of severed parts of a blood vessel and a plurality of severed blood vessels. The plurality of interwoven lengths may be configured as a tubular braid. The plurality of interwoven lengths may include a plurality of warps and a plurality of wefts, the warps featuring filaments running in one direction and the wefts featuring filaments running in an opposing direction to the warps at an angle to the warps and wherein the angle is reduced by pulling the multi-tubular device outwards and the angle is increased by pushing the multi-tubular device inwards. The multi-tubular device may be constructed from at least one of metal, plastic, nitinol, alloys of titanium and nickel, stainless steel, platinum, gold, silver, copper, zinc, silicone, ceramic, polytetrafluoroethylene (PTFE), polyethylene, urethane, nylon, polyester, polypropylene, fabric, gut and tissue graft. The elongated member may include an external surface and an internal surface, where the internal surface may be coated with at least one layer of coating. The internal connecting point or joining line may include at least one stop element for preventing displacement of a biological structure beyond the stop element deeper into the cavity. The at least one stop element may be at least one unidirectional movement prevention element configured to promote movement only in an opposite direction to the direction of insertion of the biological structure stopped by the at least one stop element. The multi-tubular device may include at least one unidirectional movement prevention element for preventing displacement of an inserted at least one biological structure away from the proximal end of an elongated member towards the distal end of that elongated member. The at least one unidirectional movement prevention element may include at least one spike. The at least one spike may be positioned substantially parallel to an elongation direction of the device. The multi-tubular device may tighten about the at least one biological structure when at least one of the ends is pulled outwards, a pushing force is eliminated and the device enters its relaxed state. A plurality of multi-tubular devices may be used in a bypass procedure. In one non-limiting example two multi-tubular devices may be used in a bypass procedure, each multi-tubular device for connecting an end of a bypass blood vessel with two cut ends of a blocked blood vessel at a respective side of the blockage, A first tube of a first multi-tubular device may be for accommodating a first end of a cut blocked blood vessel cut on a first side of a blockage, a second tube of the first multi-tubular device may be for accommodating a second end of the cut blocked blood vessel cut on the first side of the blockage and a third tube of the first multi-tubular device may be for accommodating one end of a bypass blood vessel. A first tube of a second multi-tubular device may be for accommodating a first end of the cut blocked blood vessel cut on a second side of the blockage, a second tube of the second multi-tubular device may be for accommodating a second end of the cut blocked blood vessel, cut on the second side of the blockage and a third tube of the second multi-tubular device may be for accommodating a second end of a bypass blood vessel.

A still further aspect is a method of performing a bypass procedure with a plurality of multi-tubular devices, such as for example two multi-tubular devices. The method may include providing a first multi-tubular device, cutting a blocked blood vessel on a first side of the blockage, thereby providing a first cut end and a second cut end, inserting the first cut end into a first opening of the first multi-tubular device, inserting the second cut end into a second opening of the first multi-tubular device and inserting a first end of a bypass blood vessel into a third opening of the first multi-tubular device. The method may include providing a second multi-tubular device and cutting the blocked blood vessel on a second side of the blockage, thereby providing a third cut end and a fourth cut end. The method may include inserting the third cut end into a first opening of the second multi-tubular device, inserting the fourth cut end into a second opening of the second multi-tubular device and inserting a second end of the bypass blood vessel into a third opening of the second multi-tubular device.

BRIEF DESCRIPTION OF THE DRAWINGS

The various features of the invention will best be appreciated by simultaneous reference to the description which follows and the accompanying drawings and in which.

DETAILED DESCRIPTION

Figure 1:
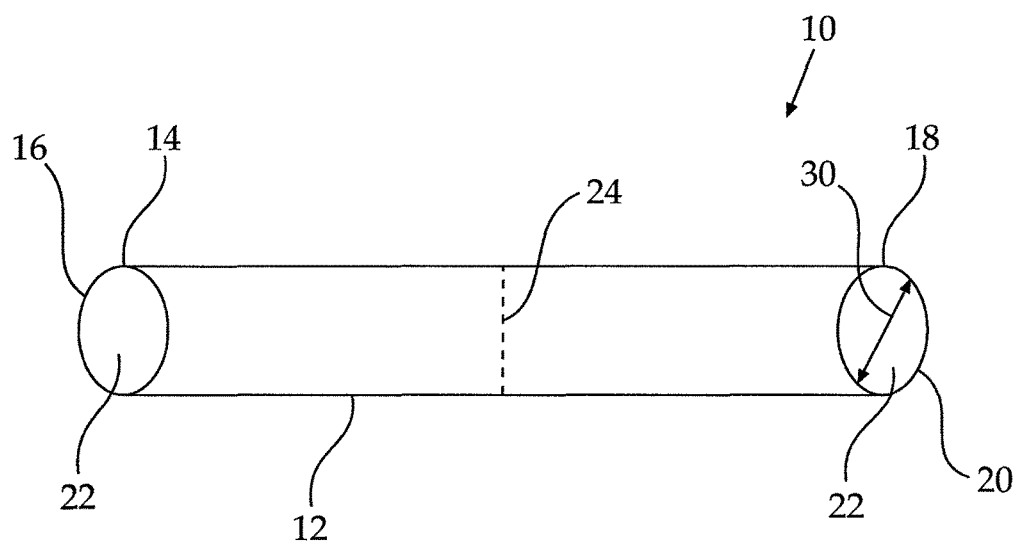
FIG. 1 shows a schematic view of a connector device according to an aspect of the present invention.

In one aspect the present invention is of a connecting device. The connecting device may be a device for joining body tissues. The device may be for joining tissues in humans, mammals and animals. The device may be for joining biological tissues found internally. In a further aspect the present invention provides a method of using a connecting device. The present invention provides uses of such a device, for anastomosis, surgery, wound treatment and a combination thereof. In a still further aspect the present invention is of a method of production of the connecting device. The present invention provides a system for replacing and/or augmenting suturing in a bypass procedure, wherein the system may include a plurality of connector devices or a plurality of parts of a connector device of the present invention. In an aspect the present invention is of a multi-tubular device for connecting body tissues. The present invention provides methods of use of a multi-tubular device. In one aspect the present invention is of a multipart device for joining body tissues. The present invention provides a method of use of a multipart device. It is envisioned that the present invention may be used in the joining of any suitable tissues and body structures in any suitable area of the body.

The device according to an aspect of the present invention may comprise an elongated member (for example an elongated tubular member), a first opening at one extremity end of the member, a second opening at a second opposing extremity end of the member and a central cavity within the elongated member for accommodating at least one biological structure. The elongated member may comprise a plurality of interwoven lengths configured for reversible radial enlargement of the member when the extremities are pushed inwards and reversible radial contraction of the member when the extremities are pulled outwards. The exposed ends of the biological structure/s and/or non-biological structures to be connected may be accommodated in the cavity of the device. The biological structures/s may be inserted into the cavity of the double open ended device, wherein each biological structure or part thereof may be inserted through an opening at a different end of the device. The device may be tightened around the biological structure/s by a pulling of the device about the open ends of the device and/or by the automatic reversal of the radial enlargement when the pushing forces on the device are removed.

The devices of the present invention provide uniform contact between the device and biological structure/s, which are to be joined and uniform contact between the exposed ends of the biological structures to be connected. There are substantially no gaps or holes in the inserted biological structure/s caused by the devices of the present invention, such as those resulting from the use of sutures. As such, there is less leaking than in suturing. Moreover, the devices of the present invention do not exert substantially any external pressure on the biological structure. The anchoring of the biological structure/s within the device may be provided by the contractible dimensions of the device, which may conform to the dimensions of the biological structure. Due to the devices not exerting pressure on the biological structure/s, the devices may prevent pressure sores and related infection. Further, the lack of pressure by the devices may avoid causing narrowing of the joined biological structure/s. Pressure may be exerted on the devices of the present invention by for example discharges or leaking from the biological structure/s. The pressure exerted by such discharges on the device may facilitate the devices holding the biological structure/s tighter, which may prevent more leaking.

The devices of the present invention are relatively facile to use and facilitate a method of joining biological tissues/s, which is fast and less time consuming than the commonly used method of suturing.

As used herein the term 'braid' may include, but is not limited to lengths and/or strips of for example filaments of suitable dimensions interwoven in a diagonally overlapped pattern.

As used herein the term 'tubular braid' may include any suitable configuration, with properties similar to a Chinese finger trap, wherein the configuration reversibly facilitates radial enlargement when the extremities are pushed inwards and reversibly facilitates radial contraction when the extremities are pulled outwards and/or pushing forces are removed. The term includes any tubular braid with suitable dimensions and suitably configured for use on a biological tissue. The term 'tubular braid', 'braided sleeve', 'tubular plait', and 'plaited sleeve' may be used interchangeably.

As used herein the term 'unidirectional movement prevention' may include, but is not limited to substantial prevention of movement in one direction, whilst allowing movement in an opposing direction.

As used herein the term 'radial enlargement' may include, but is not limited to an increase of the radius and/or diameter of a tubular structure or similar shaped structure without external addition or deletion to the original structure.

As used herein the term 'reversible radial enlargement' may include, but is not limited to a return of the size of the radius towards and/or to its original radius on removing the forces facilitating the radial enlargement. The term may include a return to a radial size which is a reduction of the radial enlargement, but which may not be the same size as the original radius.

As used herein the term 'radial contraction' may include, but is not limited to a decrease of the radius and/or diameter of a tubular structure or similar shaped structure without external addition or deletion to the original structure.

As used herein the term 'reversible radial contraction' may include, but is not limited to a return of the size of the radius towards and/or to its original radius on removing the forces facilitating the radial contraction. The term may include a return to a radial size which is an increase of the radial contraction, but which may not be the same size as the original radius.

As used herein the term 'joining' may include, but is not limited to contacting and connecting in any suitable way in order that a plurality of structures or parts thereof are attached. The term may include connecting the two parts of a biological structure resulting from severing or cutting of the original uncut biological structure, such that the joining will reform the original uncut biological structure.

As used herein the term 'biological structure' may include, but is not limited to any suitable biological tissue, which can be accommodated in the device of the present invention. The two sides of a cut biological structure, such as the two sides of one of the cuts of the blocked artery in FIG. 12 below, may be considered to be two separate biological structures.

As used herein the term 'pulling' may include, but is not limited to a tugging force applied to the device in the direction from the midline of the device towards an opening/s of the device. The term may include a pulling force applied to one section, or a plurality of sections of the device, or parts of a section of the device.

As used herein the term 'pushing' may include, but is not limited to a force applied to the device, where the force is applied in the direction from an opening/s of the device towards the midline of the device. The term may include a force applied to the device in the direction from an opening towards the second opening of the device. The term may include a pushing force applied to one section or a plurality of sections of the device or parts of a section of the device.

The principles and operation of a device, such as a connector according to the present invention may be better understood with reference to the figures. The figures show non-limiting aspects of the present invention.

FIG. 1 shows a schematic view of a device 10 according to an aspect of the present invention. In one aspect the device 10 may be a tubular open ended device. The device 10 may be flexible. The device 10 may include an elongated structure 12, which may include a first end 14 with a first opening 16 and a second end 18 with a second opening 20. The device 10 may be a hollow elongated structure with a cavity 22, which may be substantially hollow extending longitudinally between the first opening 16 and the second opening 20. The device 10 may include a joining line 24, which may be an imaginary line. The term 'joining line' 24 as used herein may include a line, a point or position/s in the device where the biological tissues and/or non-biological tissues, which are inserted in the device 10 and accommodated in the device 10, are contacted together. The joining line 24 may be positioned along the elongated structure 12 between the first opening 16 and the second opening 20. In some aspects, the joining line 24 may be at any suitable point, which may be substantially midway or which may not be midway between the two openings 16, 20. Such a device with a joining line 24 which is not at midway may be suitable when two different structures are being joined, or when a stop element is not positioned at the midline of the device.

Device 10 may be made from a flexible material, which may be constructed in a configuration such that when an object is inserted into the cavity 22 and any pushing force is removed, the dimensions of the device are such that the device may hold tightly the inserted object within the cavity 22. When a first end 14 and/or the second end 18 of the device 10 are pulled, the diameter of the device narrows to hold the inserted object/s tighter within the cavity 22. The material and configuration of the material forming the device 10 facilitates radial enlargement when the device is pushed inwards and facilitates radial contraction when the device is pulled outwards. Such radial enlargement and radial contraction may provide anchoring of a structure, such as not limited to a biological structure which is inserted into the cavity of the device. The material of the device 10 may be configured such that the radial enlargement and radial contraction are reversible when the pushing and pulling forces are absent when no structure is inserted into the cavity. The device 10 may be of a Chinese finger cuff configuration, stent-like configuration, a weave, a mesh, a network, a knit, a braid, a helically wound braid, biaxial braid, coils, spirals, knots, twists, a scaffold, a crocheted design and combination thereof or any suitable equivalent construction design. The device may be of any suitable construction design which is configured for reversible radial enlargement and reversible radial contraction. FIG. 1 shows a non-limiting example of the device 10 constructed from a tubular braid configuration. Device 10 may be made from any suitable material. The material may be biocompatible and non-toxic. The material may be a material which has sufficient properties of flexibility to impart flexibility on the device. Non limiting examples of materials which may be used include nitinol, alloys of titanium and nickel, stainless steel, platinum, gold, silver, copper, zinc, ceramic, polytetrafluoroethylene (PTFE), polyethylene, urethane, silicone, nylon, polyester, polypropylene, fabric, gut, tissue graft and combinations thereof. The device may be constructed from a tubular braid made from one material or a combination of materials. The material may be biodegradable and/or bioabsorbable. In a device which is biodegradable, the device may be metabolized or broken down by a suitable process and the resulting broken down components may be removed from the body by for example excretion. In some embodiments, wherein long term reinforcement is needed at the point of connection, the device is made from a material which is not bioabsorbable. The device material may be disposable. The device material may be absorbent or non-absorbent. The device material may be porous and may have different porosities. The device material may be configured to include interstitial spacing for relative movement of the components, such as the filaments or strips of the device.

Figure 2A:
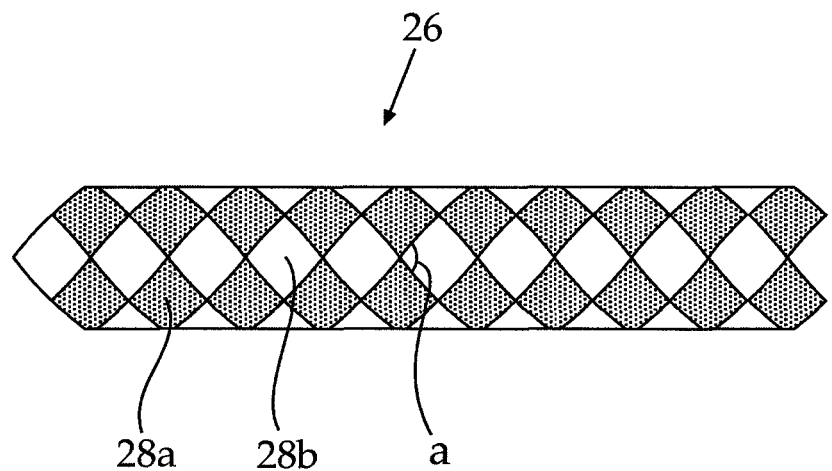
FIG. 2a shows a schematic view of a braid according to an aspect of the present invention.

FIG. 2a shows a schematic view of a braid 26 used to construct the device 10 according to an aspect of the present invention. The braid 26 may be similar to the tubular braid of a Chinese finger cuff. The braid 26 may be constructed from a plurality of parts or lengths, such as 28a, 28b, which are braided or interwoven. Individual parts 28, may be strips or tubes or threads or wires or filaments or any suitable form which may be braided or weaved and used to form a tubular braid or weave. As used herein the term 'filament' may include any suitable individual part of a braid, which can be braided, plaited or weaved. The term includes tubes, threads, wires and strips and combinations thereof. The filaments may be round, flat, ribbon, square or a combination thereof. The dimensions of the filaments 28 may determine the size and the flexibility of the device. The parts or filaments 28 may be of any suitable thickness, such that the parts or filaments 28 can be braided or formed into the reversible radial size configuration of the device. The thickness to be used will be determined and optimized for each material used. The thickness of the parts or filaments 28 may be from about 0.01 mm to about 4 mm, or from about 0.02 mm to about 2 mm, but thinner and thicker dimensions are possible. For metallic parts or filaments 28, the thickness may be determined by different factors than non-metallic parts. In one non-limiting example the thickness of a metallic filament 28 may be from about 0.05 mm to about 2 mm. The width of the filament 28 may relate to the size of the device. As such, when the size of a device is predetermined, the widths of the filaments 28 may be calculated accordingly. In some non-limiting examples the width of a filament 28 may be from about the size of the radius plus/minus up to about 20% of the device 10. In some non-limiting examples, the width of a filament 28 may be from about the size of the radius plus/minus up to about 10% of the device 10. In some aspects, the width of the filament 28 may be up to about 2 mm and may not be fixed according to the radius of the device. In one non-limiting example, the width of the filament 28 may be up to about 1 mm. The radius of the device may be increased or decreased by using a greater or lesser number of filaments 28. The length of the filament 28 may be any suitable length. The length may be determined so that the device is sufficiently long to hold the biological structure. The length may be calculated so that the device includes a sufficient number of movement prevention components to prevent the biological structure from moving in the opposite direction it was inserted in. The length may be determined so that the device will be sufficiently long to provide the needed radial expansion and contraction. The length may be calculated so that the device will be as short as possible for easy insertion of the biological or non-biological structure within the device. In addition, the length may be optimized for insertion by endoscope. In a one part device the length may be from about three times to about fifteen times the diameter of the device. In some non-limiting examples, the length may be from about seven times to about ten times the diameter of the device. In a multipart device the length of the filament may be from about two times to about eight times the diameter of the device. In some non-limiting examples the length of a filament in a multipart device may be from about four times to about six times the diameter of the device. The spring of the device may be determined by for example the properties of the materials used to make the device and the dimensions of the materials used. The spring may be a measure of the ability of the device to regain its original shape after being compressed or extended. The spring of the device is important, to facilitate a device with reversible sizing. The tubular braids used for protecting hoses and wiring, are not suitable for use in biological tissues, because the spring is not sufficient. The tubular braids designed for these other uses are not designed with a resilient spring, but are constructed so that they are flexible and can fold. This is achieved by the braiding of parts, wherein each part is made up of multiple filaments. Using a part of multiple filaments facilitates greater bending flexibility, but reduces the ability of the device to return to its initial state, thereby preventing the reversibility of the reversible contraction and expansion properties of the end device. The braid of the device of the present invention may be made from suitable parts, which are single filaments. In some non-limiting examples wherein the device of the present invention has a sufficiently large diameter, at least one individual part which includes multiple filaments may be used, providing that the resulting flexibility facilitates sufficient reversible contraction and expansion.

Figure 2B:
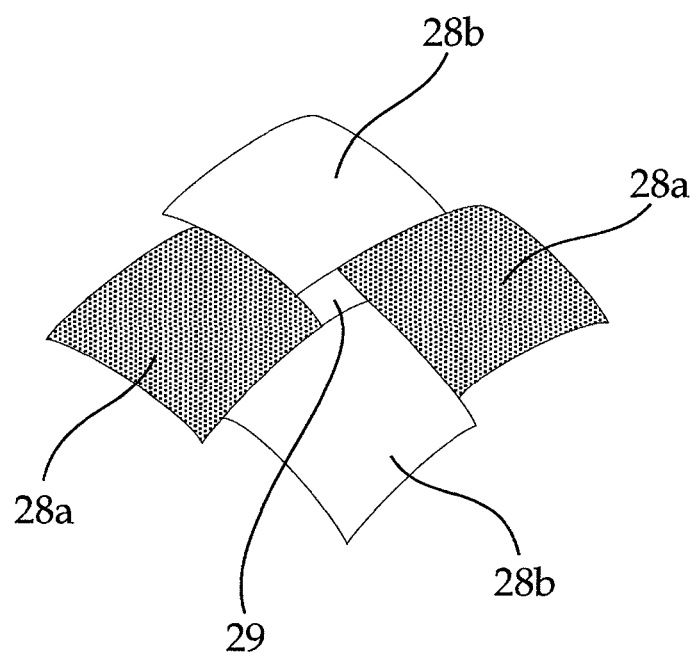
FIG. 2b shows a schematic view of a cell of a braid according to an aspect of the present invention.

Any suitable number of parts 28a, 28b may be used. The number of parts may be an even number. The number of parts may be greater than or equal to four. In one non-limiting example shown in FIG. 2a at least eight parts 28 are used. The number of filaments 28 may facilitate the shape of the device. In some aspects, such as shown in FIG. 2a in order to achieve a more cylindrical form, at least eight parts, such as eight filaments 28 may be used. Eight filaments may include four pairs of filaments. The number of filaments may be determined according to the size of the structure to be inserted into the device. For a structure with a larger radial diameter more filaments may be used than for a structure with a smaller radial diameter. The diameter of the device may be greater than 1 mm. In an aspect, wherein the device of the present invention is used for accommodating a biological structure which is tubular in shape, such as for example a blood vessel, the device may be constructed in a similar shape to the biological structure. In the device 10 of tubular design, the lengthways strips, or filaments, or the strips, or filaments running in one direction may be referred to as 'warps' and the strips, or filaments positioned over and under the warps and running in an opposing direction at an angle to the warps may be referred to as 'wefts'. The angle between the warps and wefts may be changed by pulling and pushing the ends of the device. When the angle 'a', between the warp and weft filaments is reduced by pulling the device, the radius and diameter 30 of the tubular design is reduced. When the angle 'a', between the warp and weft strips or filaments is increased by pushing the device inwards, the radius and diameter 30 of the tubular design is increased. As used herein the term 'cell' may refer to part of the braid featuring four filaments 28a, 28b positioned over and under each other with one spacing 29 in the center and as shown in FIG. 2b.

Figure 3A:
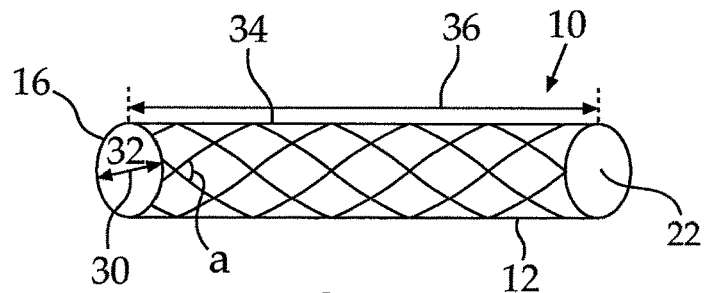
FIGS. 3a, 3b, 3c and 3d show schematic views of a connector device in different states according to an aspect of the present invention.
Figure 3B:
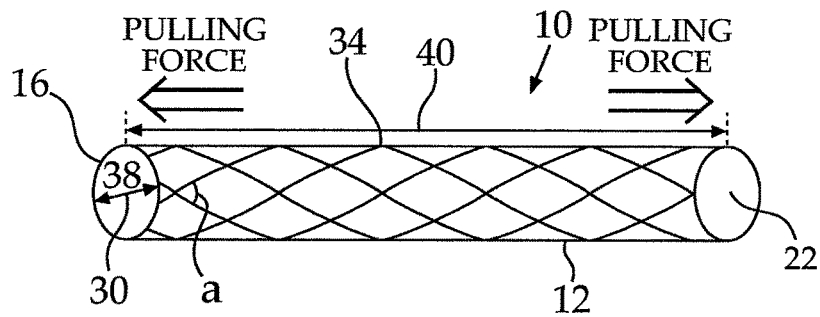
Figure 3C:
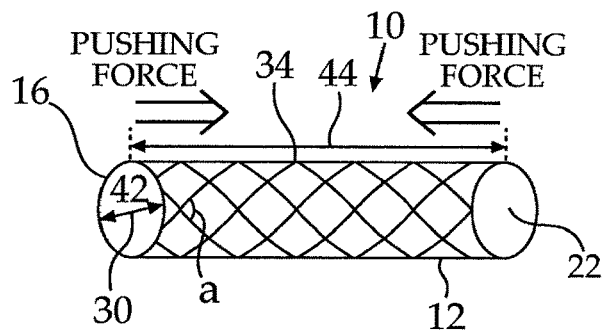

The diameter 30 of the device 10 may be changeable. The device 10 may have at least three different states, a relaxed state as shown in FIG. 3a, a pulled state as shown in FIG. 3b and a pushed state as shown in FIG. 3c. A 'relaxed state' refers to a state wherein the device is not pulled or pushed at its extremities and/or along its length. A 'pulled state' refers to the device wherein at least one of the extremities and/or a suitable part along the length of the device is pulled. A 'pushed state' refers to the device wherein at least one of the extremities and/or a suitable part along the length of the device is pushed. In FIG. 3a wherein the device 10 is in a relaxed state, the diameter 30 of the elongated member 12 and cavity 22 may be a first size 32 and the length 34 of the elongated member 12 may be a first size 36. The angle between warp and weft is 'a'. In FIG. 3b wherein the device 10 is in a pulled state, the diameter of the elongated member 12 and cavity 22 may be substantially reduced resulting in a reduced diameter 38 and the length 34 of the elongated member 12 may be increased to increased length 40. The angle 'a' between the warp and weft is decreased compared to the angle 'a' in the relaxed state. FIG. 3b shows the direction of a pulling force. In a pushed state, shown in FIG. 3c, the diameter 30 of the member 12 and cavity 22 may be substantially increased to increased diameter 42 and the length 34 of the elongated member 12 may be reduced to reduced length 44. The angle 'a' between the warp and the weft is increased compared to the angle 'a', in the relaxed state. The type of configuration used to construct the device 10 may include any suitable construction, which will facilitate such a substantially reversible change in size as shown in FIGS. 3a-3d. FIGS. 3a-3d are not to scale.

Figure 3D:
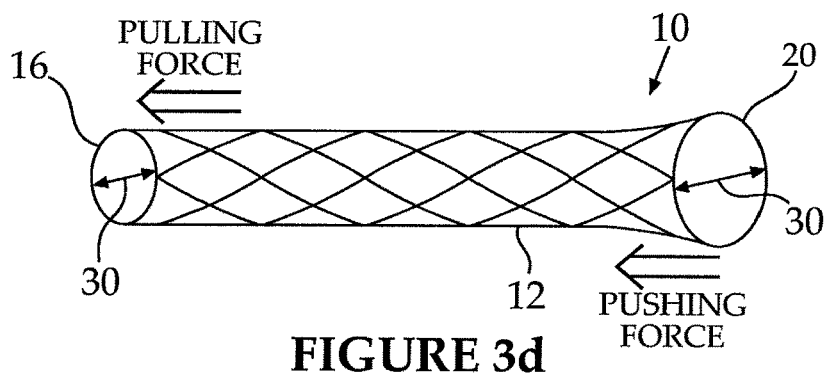

The device 10 may be used for application to blood vessels, lymphatic vessels, ligaments or nerves or any other suitable biological structure of any suitable size. The device 10 may be made of wider filaments 28 and/or more filaments 28 to achieve a wider diameter 30 suitable for larger vessels. The device may be constructed with a diameter in its resting state such that it is suitable for connecting structures with a diameter of from about 0.5 mm to about 50 mm. In some non-limiting examples, the device may be used to connect smaller or larger structures and the diameter of the device in its resting state will be based on the dimensions of these structures to be inserted therein. In some non-limiting examples, the device may be used to connect structures with a diameter of from about 2 mm to about 9 mm. The same connector device 10 may be used to connect structures such as blood vessels of different sizes. This may be achieved, as the internal dimensions of the device 10 may be adjusted by pulling and pushing the device at or near to the relevant ends of the device as shown in FIG. 3d in order to accommodate structures of different dimensions. FIG. 3d shows a device 10, with opening 16 having a diameter 30 which is smaller than the diameter 30 at opening 20. The connector devices 10 of the present invention may be designed and constructed in a range of dimensions, to be suitable for different biological structures and different ranges of size of biological structures.

The device 10 may have a permanent set put into in so that it is normally open with the larger diameter associated with the 'pushed state' described above. In such a non-limiting example when it is pulled, the device will collapse down to the diameter of the biological structure inserted within the device. Optionally, the device 10 may have an over tube which is slideable and which facilitates the 'pulled state' and 'pushed state'.

The length 34 of the device 10 of the present invention may be adjusted according to the end use of the device 10 and according to the type and length of the biological vessel/s to be connected. The length of the device may be determined as described hereinabove for determining the length of a filament. The length of the device may be determined so that it is long enough to hold the biological structure. The length may be calculated so that the device includes a sufficient number of movement prevention components to prevent the biological structure from moving away from the joining line by moving in the opposite direction it was inserted in. The length may be determined so that the device will be sufficiently long to provide the needed radial expansion and contraction. The length may be calculated so that the device will be as short as possible for easy insertion of the biological or non-biological structure within the device. In addition, in one non-limiting example the length may be optimized for insertion of the device into the body by endoscope. In a one part device the length of the device may be from about three times to about sixteen times the diameter of the device. In some non-limiting examples the length of the device may be from about seven times to about ten times the diameter of the device. In a multipart device the length of the device may be from about two times to about eight times the diameter of the device. In some non-limiting examples the length of a part of a multipart device may be from about four times to about six times the diameter of the device.

Referring back to FIG. 1, the ends of the device 14 and 18 are constructed so that the individual filaments or strips do not stick out at the end. Non-limiting examples of suitable finishes to the ends 14 and 18 are folding of the filaments into the tubular braid, tucking the ends of the filaments into the braid, gluing down the ends, stitching the ends or a combination thereof. Tubular braids constructed for protection of hoses or wiring do not include such a finish and the ends can catch, causing damage in a biological environment.

Figure 4A:
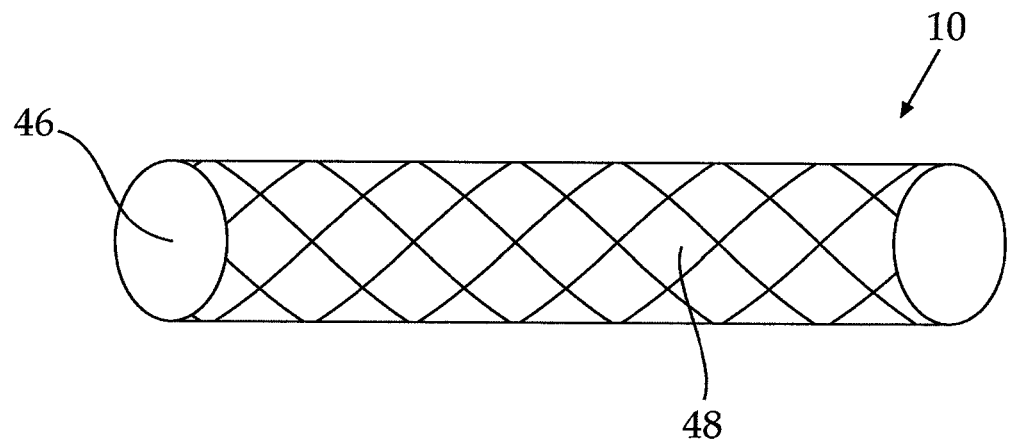
FIG. 4a shows a schematic view of the surfaces of a connector device according to an aspect of the present invention.
Figure 4B:
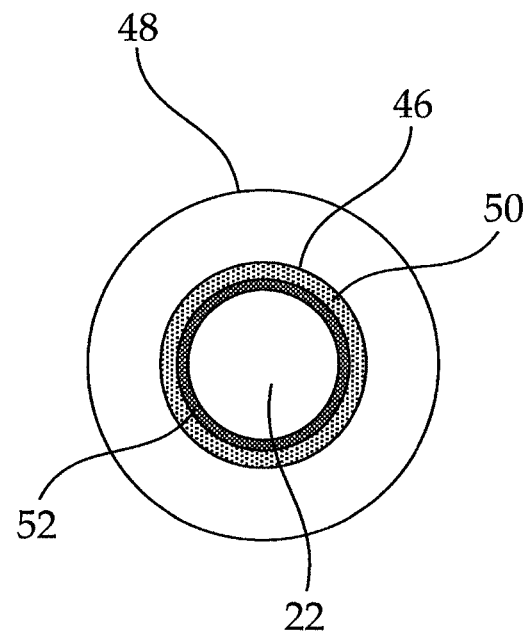
FIG. 4b shows a front view of the surfaces of a connector device according to an aspect of the present invention.

The device 10 may include an inner surface and an outer surface. FIG. 4a shows schematically the inner surface 46 and the outer surface 48 of the device 10 according to an aspect of the present invention. The inner surface 46 and the outer surface 48 may have the same structure or may have different structures. FIG. 4b shows a front view of the surfaces of the device according to an aspect of the invention. The inner surface 46 and/or the outer surface 48 may be coated with at least one layer of coating 50. The at least one layer of coating 50 may include one substance or a combination of substances. The at least one layer of coating 50 may include a glue, an adhesive, sealant or any suitable adhering substance. The glue may promote adhering the ends to be joined of the inserted biological structures and/or non-biological structures. The glue may facilitate temporary sticking together of the structures to be joined until the structures heal and join. In some non-limiting examples, the glue may be applied about the joining line of the inner surface of the device in order to facilitate bonding of the cut ends. Non-limiting examples of suitable glues for use in the present invention include surgical glues, fibrin sealants, collagen based compounds, glutaraldehyde glues and hydrogels. The at least one layer of coating 50 may include an antibiotic or any other suitable antibacterial substance. The at least one layer of coating may include at least one substance for promoting healing, a therapeutic agent, an anticlotting substance, a clotting substance, a vitamin, an antioxidant, an anti-inflammatory agent, an anesthetic agents, an anti-coagulant, an anti-restenosis agent, a thrombosis agent, an immunosuppressant agents, a dye, a movement retardation composition or combination thereof. The at least one layer of coating 50 may be covered with at least one release liner 52. The release liner 52 may prevent the coating from sticking before application and use of the device. The at least one release liner 52 may be removed prior to use. The device may include a plurality of release liners, such as, but not limited to two release liners 52, a release liner 52 for each part, or section, or half of the device. Each part or half of the device may be defined from the joining line to an open end of the device. Prior to insertion of a biological structure, only the release liner 52 covering the part of the cavity of the device into which the biological structure is to be inserted may be removed. The inner surface 46 and/or the outer surface 48 may be coated with a different at least one layer of coating. In one non-limiting example, the inner surface 46 of the device may be coated or partially coated with a suitable glue and the outer surface 48 of the device may be coated with at least one therapeutic agent. The outer surface 48 may be coated with at least one layer of coating to result in a smoother outer surface 48. In some non-limiting examples, the outer surface 48 may not include at least one layer of coating.

Figure 5A:
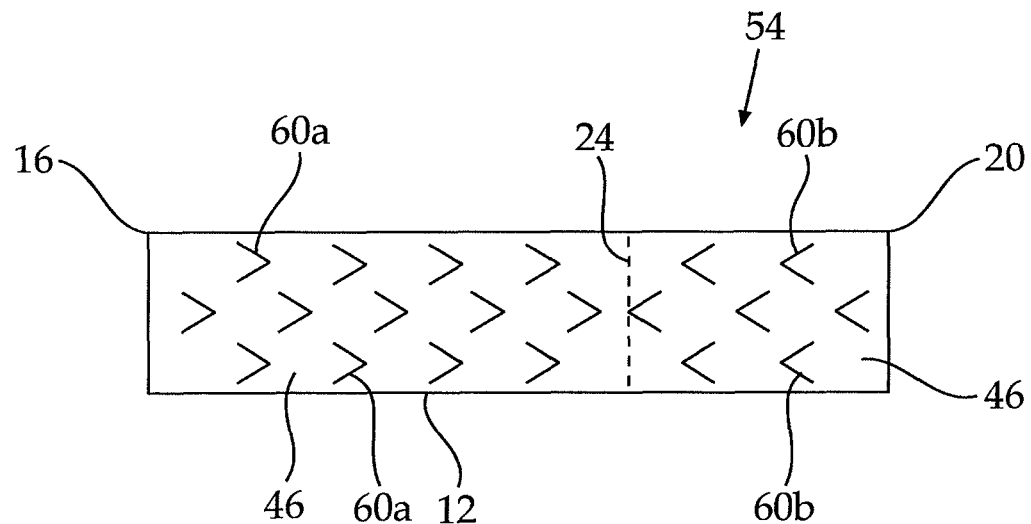
FIGS. 5a and 5b show schematic views of a movement prevention means according to aspects of the present invention.

FIG. 5a shows schematically a movement prevention means 54 according to an aspect of the invention. The device 10 may include a movement prevention means 54. In one non-limiting example the movement prevention means is a friction means for imparting and/or increasing friction of the inner surface 46 of the device 10, such that movement of the biological structure in contact with the device 10 is hindered and/or prevented, once the biological structure has been inserted and the device 10 fitted around the biological structure and configured in its connecting state. The movement prevention means 54 facilitates the device 10 being held securely about the biological structure. All parts of the device 10 may include the friction means 54 or only certain parts of the device 10 may include the friction means 54. In some aspects, only the part of the material which forms the interior surface 46 of the device 10, which may contact a biological structure for joining the biological structure, may include a means for imparting friction 54 on the device 10. The movement prevention means 54, may be unidirectional, such that a body vessel or structure may move freely against the inner surface 46 of the device 10 in one direction, but which may substantially not be displaced when moved against the means 54 in an opposing direction from the direction it was inserted.

The movement prevention means 54 may be disposed in device 10 shown in FIG. 1, such that it facilitates movement into the cavity 22 of the device 10 from the direction of the first opening 16 towards the joining line 24 and prevents movement out of the cavity 22 of the device 10 in the direction of from the joining line 24 towards the first opening 16 of a structure inserted through the first opening. At the second opposing opening 20 and in a second section of the device the movement prevention means 54 may be disposed in an opposite direction or in a different way, such that it facilitates movement in a direction from the second opening 20 towards the joining line 24 of the device 10 and opposes movement in the direction of from the joining line 24 towards the second opening 20 of a structure inserted through the second opening. Movement prevention means 54 may include any suitable abradant and/or protrusions, which may include any promoter of uni-direction. Non-limiting examples of uni-direction movement prevention means include directional ramps with attached teeth, hooks, spikes, prongs or notches, directional orientated spikes or any other suitable structure and combinations thereof.

Figure 5B:
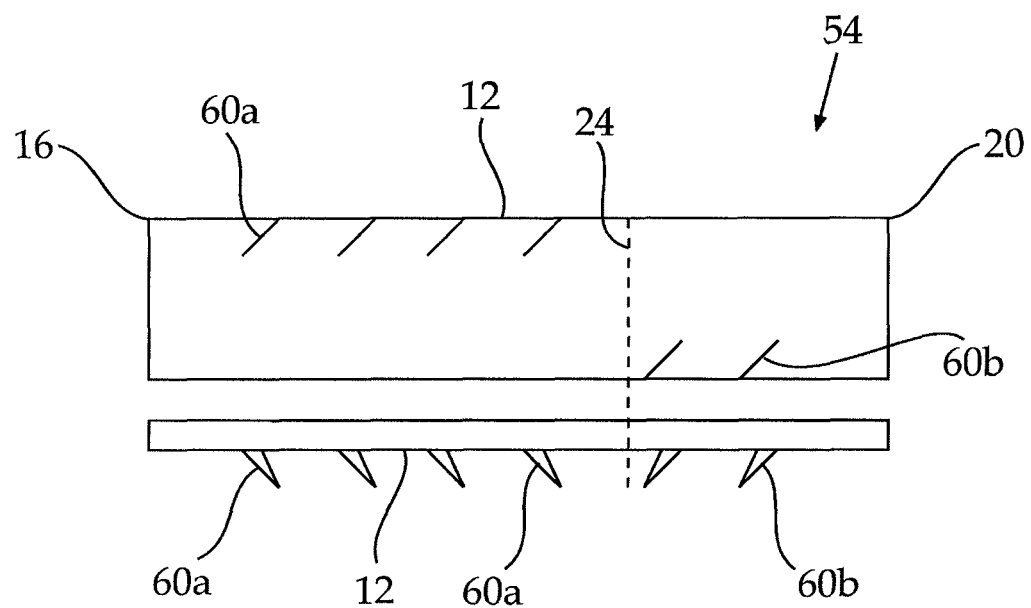

The movement prevention means 54 shown in FIG. 5a and FIG. 5b features protrusions, which may be a plurality of spikes 60 disposed along the inner surface 46 of the device 10. The spikes 60 are disposed pointing in one direction 60a in a first section of the device from the first opening 16 until the joining line 24 and the spikes are configured pointing in an opposing direction 60b in a second section of the device from the second opening 20 until the joining line 24. It is envisioned that any alternative suitable movement prevention means 54 may be disposed in a similar manner as shown in FIG. 5a and FIG. 5b. The movement prevention means 54 may be disposed uniformly or in spaced apart relation along at least one surface of the device 10. The movement prevention means 54 may be positioned so that the means 54 is substantially parallel and in line with a biological structure or other structure inserted into the device. The size of the spikes may be any suitable dimensions that facilitate prevention of movement in one direction. In one non-limiting example the spike may be constructed on a filament and from a filament such that the size of the spike's protrusion is about the same size as the thickness of the filament. The spike may bend downwards into the cavity of the device. The number of spikes may be determined according to the strength of the material from which the device is constructed and the strength of the resulting device. A filament may include one spike or a plurality of spikes. A filament may include one spike per cell. The spike/s may be positioned at an angle to the filament. The angle may be determined in order that when braided the spikes are substantially parallel with the device, such as substantially parallel with the elongation direction of the device and the inserted biological structure. Substantially parallel positioning of the spikes in relation to the resulting connector device and inserted biological structure or other inserted structure may facilitate effective functioning of the spikes as unidirectional movement prevention means. In some examples the spikes may be applied to the connector device after the device has been braided. In some examples the spikes may be applied to the filaments before braiding. In some examples, a filament may include up to about 3 spikes along the width of the filament. In one non-limiting example the distance between the peaks of two neighboring spikes is about 0.4 mm, the height of the spike from the base to the peak is about 1.0 mm and the thickness of the spike is about 0.05 mm. The base of a spike may be in line with the peak/s of the spike/s in a row behind. Conversely, the peaks of a spike may be in the same line as the base of the spike/s in the next row in front. FIG. 5b shows two views of a device according to an aspect of the present invention with spikes 60a, 60b applied along the edge of the sides of the filaments. The spike/s may be applied at a position on a filament such that the device spike position does not overlap or will not overlap a second filament and so that the resulting device spike does not have to penetrate through a second filament to be positioned in the inner surface of the device. The spike/s may be applied as cuts so that the cut edge can be pushed downwards forming a spike which is parallel to the braided device. In a non-limiting example wherein each filament includes one spike per cell, and eight strips are used to form the tubular braided connector device, the resulting device may include multiple lines of eight spikes parallel to the tubular braided device. In some aspects, the material from which the device 10 and/or the inner surface 46 of the device 10 is constructed may impart unidirectional movement prevention.

Movement prevention means 54, such as, but not limited to spikes 60 may be applied to a surface of the device 10 or may be formed from a partial perforation or partial cutout of the device. The perforation may be a superficial perforation or a perforation all the way through the surface of the filament of the device. In one example, the cutout may be two sides of a triangular or pointed spike shape, such that the base of the triangle is formed from and in the filament and the sides of the pointed spike can freely protrude from the fixed base of the filament. In an alternative example, the cutout may be a single straight or angled cut. The spike may be cut out by any suitable technique, such as but not limited to using a laser or puncher. A stitch or equivalent may be introduced about the perforation or cutout in order to maintain the dimensions of the spike.

Figure 6A:
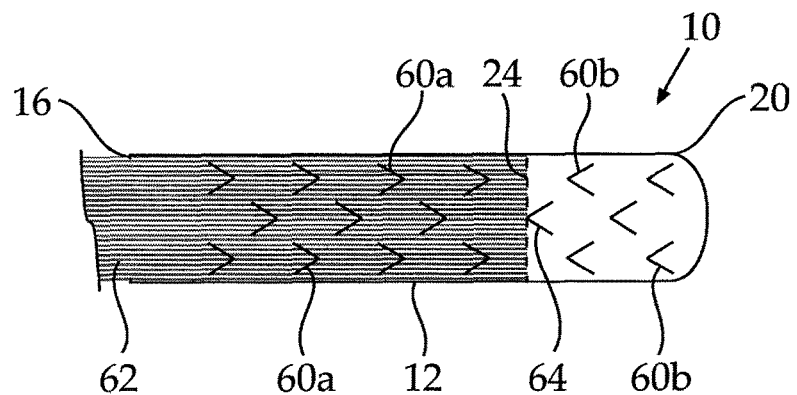
FIG. 6a shows a cross-sectional view of a device with a stop element according to an aspect of the present invention.

The device 10 of the present invention may include elongated member 12 of a length of braided material in a form which provides an inner cavity 22 capable of accommodating a biological structure 62, such as a blood vessel 62 as shown schematically in FIG. 6a. FIG. 6a shows a cross-sectional view of a device 10 which features at least one stop element 64 for positioning biological structure 62 and stopping further insertion deeper into the device 10. The at least one stop element 64 may be provided by the movement prevention means 54. In the example shown in FIG. 6a, the at least one stop element 64 may be at least one unidirectional spike 60. The spikes 60a are configured to promote insertion of biological structure 62 to a position about the joining line 24 for contact with a second structure to be inserted and connected with the first biological structure 62. When the biological structure 62 has traversed over spikes 60a and reaches spikes 60b, the opposing spikes 60b, prevent further insertion or movement into the device. Depending on the location of the spikes 60a and 60b, first inserted biological structure 62 may be inserted up to the joining line 24, which may or may not be midway along the elongated member depending on the arrangement of spikes 60a and 60b. The first opposing spikes 64 may define a position within the elongated member 12 until which the biological structure 62 can be inserted, but wherein the biological structure 62 cannot be inserted passed this at least one stop element 64. Whilst FIG. 6a shows the at least one stop element 64 is at least one spike promoting insertion from opening 20 into the cavity, this is not intended to be limiting. In an example, wherein a structure is first inserted through opening 20 into the cavity of the device 10, the at least one stop element 64 may be at least one spike, such as the first encountered spike which is configured to promote insertion from the opening 16 into the cavity in the direction toward the joining line 24. In an alternative example, two biological structures may be inserted simultaneously. In such an example, if the two biological structures are the same size, the stop element may be the midline of the elongated member 12.

Figure 6B:
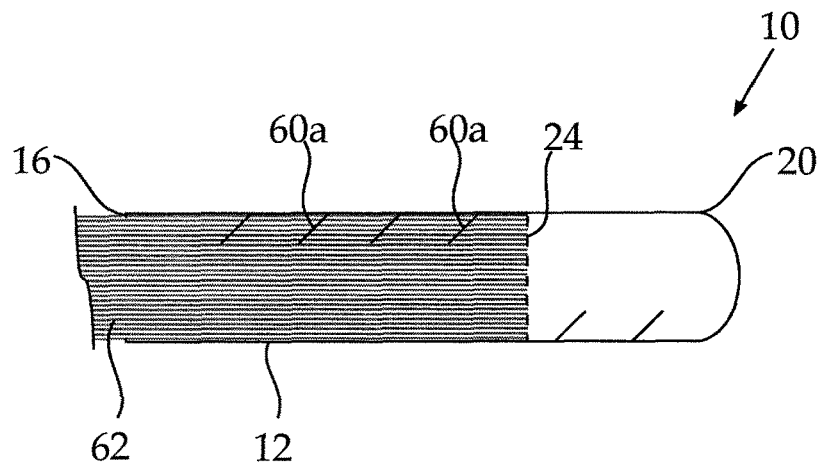
FIG. 6b shows a cross-sectional view of a device with a stop element according to an aspect of the present invention.
Figure 6C:
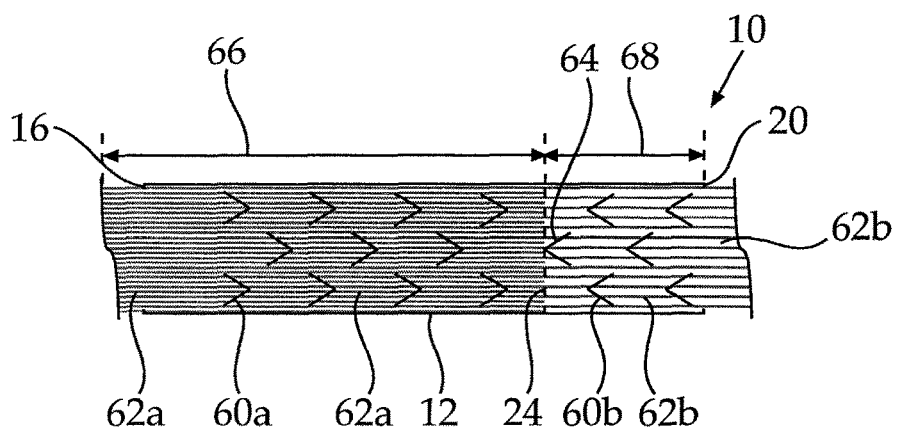
FIG. 6c shows a cross-sectional view of a device with two biological structures inserted in the device according to an aspect of the present invention.

FIG. 6b shows a cross-sectional view of a device 10 which features filaments with only one spike applied at the edge of each filament. FIG. 6c shows schematically a cross section of a device 10 connecting together two biological structures 62a and 62b according to an aspect of the present invention. FIG. 6c shows at least one stop element 64 for positioning biological structure 62a and stopping further insertion deeper into the device 10. The at least one stop element 64 may be provided by the movement prevention means 54, which may be at least one unidirectional spike 60.

A first structure 62a is inserted through opening 16 until at least one stop element 64. The device 10 accommodates the biological structure 62a in a first section of the device 66, wherein the first section 66 can be defined from the opening 16 until the stop element 64. The second structure 62b, which may be a different biological structure or a second part of the same biological structure as 62a may be inserted through the opening 20 until it contacts the inserted biological structure 62a. The device 10 accommodates biological structure 62a in the first section of the device 66, the first section 66 extending from the opening 16 until the at least one stop element 64 positioned at the joining line 24 and biological structure 62b in a second section of the device 68, wherein the second section may be defined from the opening 20 until the contacted biological structure 62a, which is disposed at the least one stop element 64 at the joining line 24.

In an alternative aspect not shown in the figures, the device 10 may include at least one additional stop element. Non-limiting examples may include a stop element configured by a narrowing of the device 10 of the present invention, such as a narrowing of the wall surface 46, for example the device including a rim on the wall at the intended joining line 24.

The at least one stop element 64 may be a permanent part of the device 10 of the present invention. The device 10 may include only one stop element 64 or a plurality of stop elements 64. In some aspects, each filament may include at least one stop element or two stop elements. In a non-limiting example wherein eight filaments are used, the device may include eight or sixteen stop elements.

Figure 7:
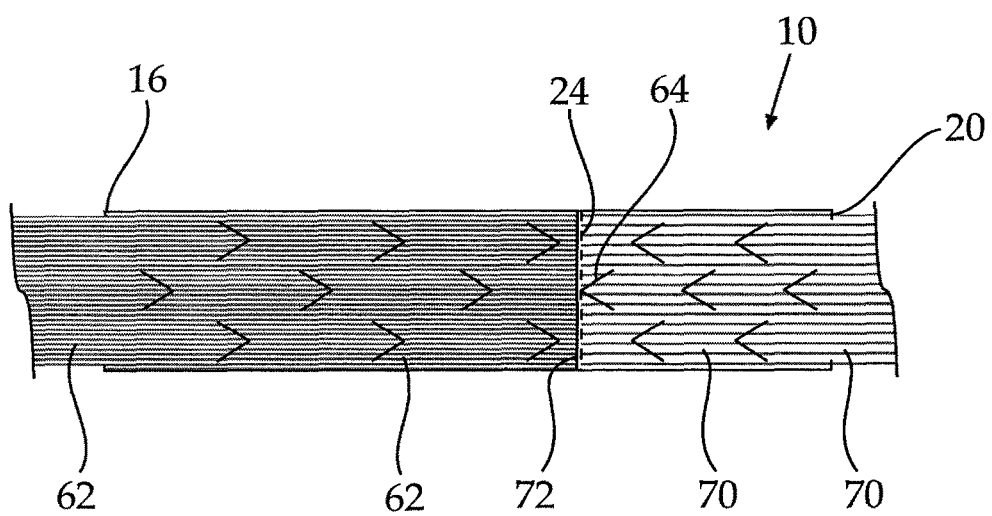
FIG. 7 shows a schematic view of a device connecting a biological structure and a non-biological structure according to an aspect of the present invention.

In some aspects, one section of the device of the present invention may be attached to a biological structure and a second section of the device may be attached to a different structure, which may be a biological structure or which may be a non-biological structure or an external biological structure. The term 'non-biological structure' as used herein may include any structure which is not found naturally in a human or animal body and/or whose source is not biological. Non-limiting examples of non-biological structures may include catheters, tubes, wires, inlets of machinery, outlets of machinery and combinations thereof. The term 'external biological structure' as used herein may include any structure, which may be biological taken from an external source from the host. Non-limiting examples of external biological structures may include biological structures or parts thereof from a different host or grown in vitro or grafts for transplanting. FIG. 7 shows schematically a device 10, connecting a tube 70 to a biological structure 62 according to an aspect of the present invention. The tube 70 may be inserted through opening 20 until the stop element 64 (which in this embodiment of device 10 is at the midline of the device). The at least one stop element 64 may be provided by the movement prevention means as shown in FIG. 7. The movement prevention means as shown in FIG. 7 is not meant to be limiting and the at least one stop element 64 may be provided by a movement prevention means 54 as shown in FIG. 5b. The biological structure 62 may be inserted through opening 16 until the first inserted end of the biological structure 62 is contacted with the first inserted end of tube 70. The radius of the tube 70 may be different from the radius of the biological structure 62, such that if the radius of the tube 70 is less than the radius of the biological structure 62, on contact between the tube 70 and the biological structure 62, the tube 70 or part thereof may be inserted into the biological structure. In a non-limiting example wherein the radius of tube 70 is greater than the radius of the biological structure 62, the tube 70 may engage the first inserted end 72 of the biological structure 62. Alternatively, the first inserted end of tube 70 may just touch or contact the biological structure 62 without insertion into or accommodation of the biological structure. In one non-limiting example the tube 70 may be a tube of a device, such as a catheter. In such an example the device may provide connection of a biological structure to a catheter.

In some aspects, the present invention provides a system of a plurality of devices 10 for connecting at least one biological structure. In one non-limiting example two devices may be used, such as, but not limited to for use in rejoining a tissue cut into four parts.

Figure 8A:
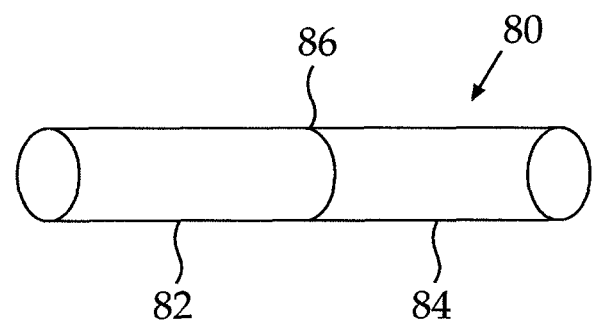
FIG. 8a shows a schematic view of a multipart connector device according to an aspect of the present invention.
Figure 8B:
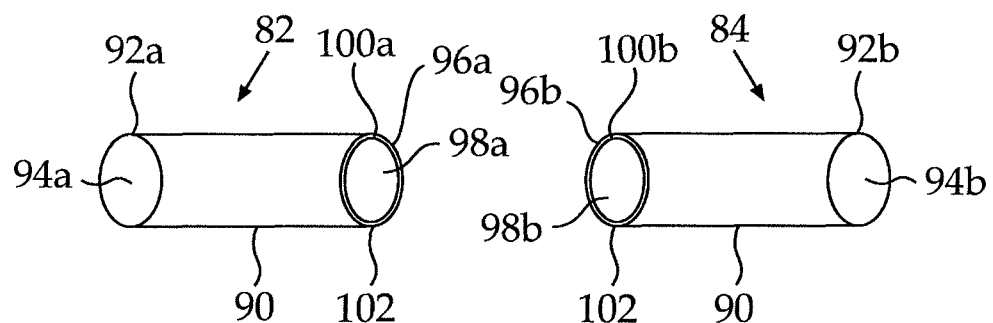
FIG. 8b shows a schematic view of two parts of a multipart connector device according to an aspect of the present invention.
Figure 8C:
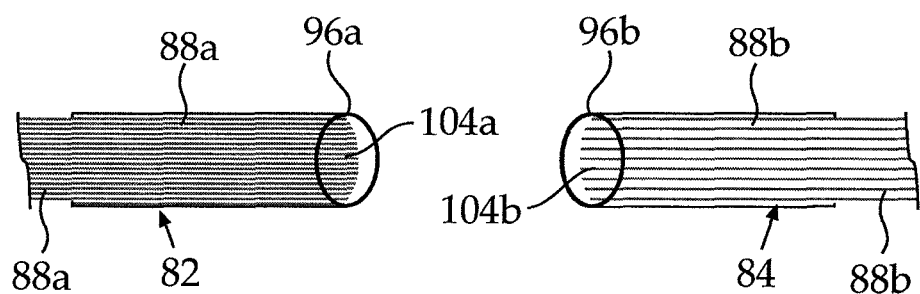
FIG. 8c shows a schematic view of biological tissues inserted into two parts of a multipart connector device according to an aspect of the present invention.

In some aspects, the device may be a multipart device. FIG. 8a shows schematically a multipart device 80 according to an aspect of the present invention. In such an aspect, the multipart device 80 of the present invention may include two separate parts 82, 84. FIG. 8a shows the two parts 82, 84 of the multipart device 80 in a connected state, wherein the two parts are attached to each other by attachment means 86. FIG. 8b shows each separate part 82, 84 of the multipart device 80. Each separate part 82, 84 is similar to one section of the one part connector device 10 from an opening of the device until the joining line as described hereinabove and shown in FIGS. 1-7. Each separate part 82, 84 is for accommodating one biological structure 88 or one part thereof as shown in FIG. 8c. Each separate part 82, 84 of the multipart device may be attachable one to each other to form an attached device 80. Each part of the multipart device 82, 84 may be substantially the same.

As shown in FIG. 8b each separate part 82, 84 includes a tubular elongated member 90 constructed from a material configured so that the diameter of the device can reversibly change by pulling and/or pushing the ends of the device and as previously described hereinabove. Suitable constructions may include a braid, tubular braid, weave, mesh and network and combinations thereof as detailed hereinabove. Each part of the multipart device includes an elongated member 90, which may be of tubular construct with a distal end 92 with a first opening 94 through which a structure/s 88, such as a biological structure to be joined, may be inserted and a proximal end 96 with a second opening, a proximal opening 98. The proximal opening 98 may differ from the openings 16, 20 of the one part connector device described hereinabove. The opening 98 at the proximal end may include one part of an attachment means 100a, which may be attachable to a corresponding attachment means 100b of a second part 84 of the multipart connector device 80. Non-limiting examples of suitable attachment means include hooks, female and male part connectors and glue. The opening 98 at the proximal end may also include at least one suitable stop element 102 for holding an inserted structure 88 at the correct position. Each part of the multipart device 82, 84 may include unidirectional movement prevention means as described hereinabove. Each part 82, 84 will only include unidirectional moment prevention means configured for promotion of movement in the direction of insertion into the cavity and for preventing displacement away from the proximal end 96 towards the distal end 92.

Referring to FIG. 8b and FIG. 8c a first biological structure 88a or part of a biological structure, such as for example a blood vessel may be inserted through the first opening 94a at the distal end of a first part 82 of the multipart device into the cavity of the device, until the first inserted end of the biological structure 104a, which may be a severed end 104a, reaches the second opening, the proximal opening 98a of the first part 82 of the device. The proximal opening 98a may include a suitable stop element for holding the biological structure at the correct position. The proximal opening 98a may include one part of an attachment means 100a. A second biological structure 88b or part thereof may be inserted in a similar manner into a second separate part 84 of the multipart device. The attachment means 100a of the first part 82 of the device may be connected to the second part 84 of the device 80 by attachment to the corresponding attachment means 100*b* on the second part 84 of the multipart connector device 80. Connection of the two parts 82, 84 of the device 80 may facilitate joining, such as for example end to end joining of the two biological structures 88*a*, 88*b*. Optionally, a non-biological structure can be inserted into at least one part of the device 82, 84 in order to connect a non-biological structure to a second structure, which may be a biological structure. In a non-limiting example, the two parts 82, 84 may be used separately without attachment of the two parts directly together. In such an example, the attachment means may be configured for attaching to a standalone attachment means, such as a clip or a clamping means. In a non-limiting example wherein the attachment means 100*a*, 100*b* are configured for attachment to a clip, the attachment means 100*a*, 100*b* may not facilitate attachment of the two parts 82, 84 together and the two parts 82, 84 may be separate connector devices. Alternatively, the attachment means 100*a*, 100*b* may be configured for both attachment of the two parts of the multipart device together and for attachment to at least one clip. A multipart connector device 80, wherein the two parts 82, 84 include attachment means 100*a*, 100*b*, which are configured for attaching to at least one clip or clamp, may be used in a bypass procedure.

Figure 9:
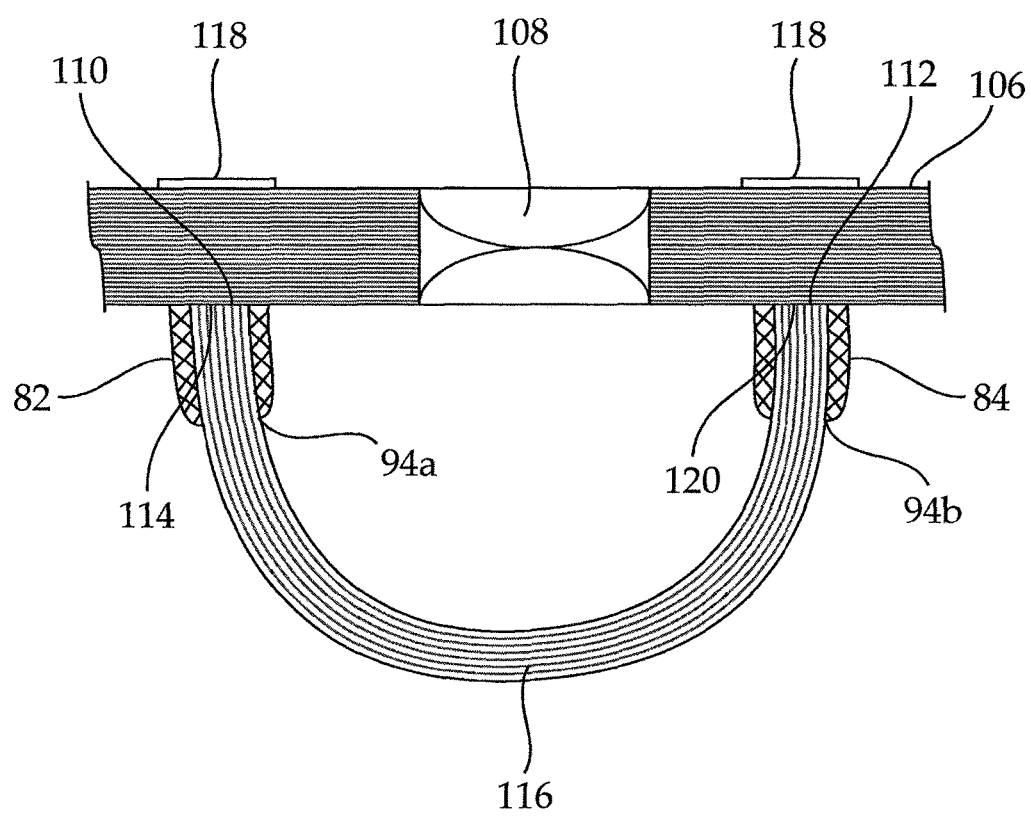
FIG. 9 shows a schematic view of a device connecting vessels in a bypass procedure according to an aspect of the present invention.

In one aspect, the device of the present invention, such as a multipart connector device 80 may be for connecting more than two biological structures, such as in a bypass for promoting optimal blood flow in a blocked blood vessel. The multipart device 80 may be part of a system for replacement of and/or augmenting suturing in a bypass procedure. FIG. 9 shows schematically parts of a multipart device 82, 84 of the present invention for use in bypassing according to one aspect of the invention. A biological structure, such as a blood vessel, for example an artery 106 may have a blockage 108. A plurality of incisions may be made in the biological structure, such as a first incision on a first side of the blockage before the blockage 110 and a second incision on a second side of the blockage after the blockage 112. One end 114 of a biological structure such as a blood vessel 116, which may be from any suitable source, such as but not limited to a blood vessel from a leg or other part of the patient, a blood vessel from a donor person, mammal or animal, and which may be used to bypass the artery 106 may be inserted into the opening 94*a* of a first tubular member of a first part 82 of a multipart connector device 80 until it reaches the proximal end of the first tubular member of the first part 82 of the device or a stop element. The blood vessel first end 114 accommodated in the first part of device 82 may be positioned such that the cut inserted end 114 of the blood vessel 116 is lined up and contacted with the first incision on the first side of the blockage before the blockage 110. One or a plurality of clamps or rings or clips 118 or any suitable means may be positioned about the blocked artery 106, such as but not limited to at or near the first incision. The clip 118 may be positioned so that it can hold the first part 82 of the device with the inserted blood vessel 116 in contact with the region of the first incision 110 of the blocked artery 106 in order that blood can flow through the incision 110 into and through the end 114 of the inserted blood vessel and into the blood vessel 116. The clip 118 may hold the first part 82 of the device about an attachment means on the first part of the device 82 which is configured for attachment to the clip or clamp 118.

A second end 120 of the bypass blood vessel 116 may be inserted into the opening 94*b* of a second tubular member of a second part 84 of a multipart connector device 80, wherein insertion may be until the proximal end of the second tubular member of the second part 84 of the multipart device or a stop element. The blood vessel second end 120 accommodated in the second part of the device 84 may be positioned such that the cut inserted end 120 of the blood vessel 116 is lined up and contacted with the incision after the blockage 112. One or a plurality of clamps or rings or clips 118 or any suitable means may be positioned about the blocked artery 106, such as but not limited to at or near the second incision 112. The clip 118 may be positioned so that it can hold the second part 84 of the multipart device with the inserted blood vessel 116 in contact with the region of the second incision 112 of the blocked artery 106 in order that blood can flow from the blood vessel 116 through the end 120 of the inserted blood vessel and through the incision 112 into the artery 106. The clip 118 may hold the second part 84 of the device about an attachment means on the second part of the device, which is configured for attachment to the clip or clamp 118.

When both ends 114 and 120 of the bypass blood vessel 116 are inserted into the two parts 82, 84 of the multipart connector device 80 and the multipart connector device parts 82, 84 are maintained in a correct position by a suitable means 118, blood can flow in the artery from before the blockage to after the blockage via the bypass blood vessel 116. The direction of flow is not meant to be limited and the opposite direction to that described here may also apply.

Figure 10:
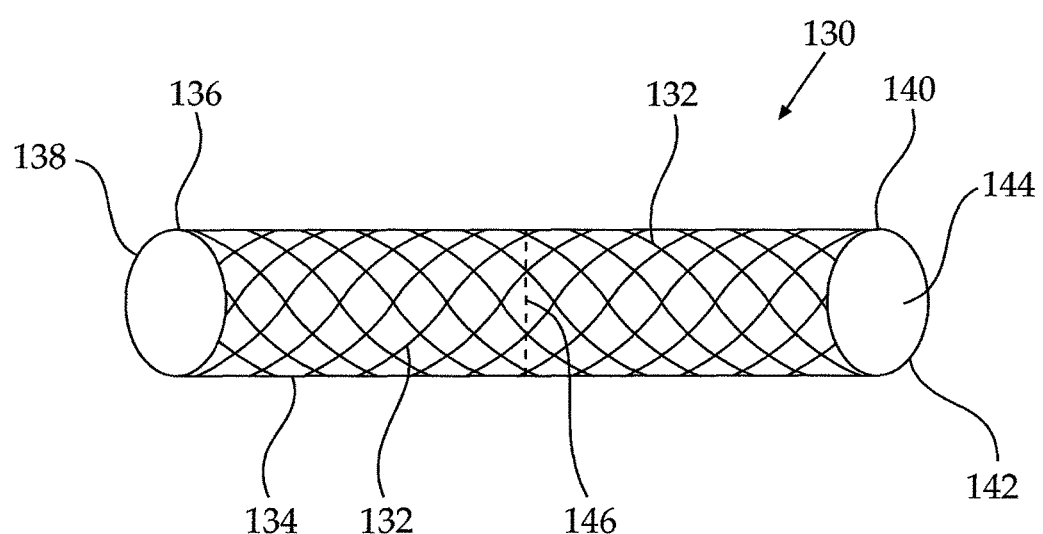
FIG. 10 shows a schematic view of a device with a net design according to an aspect of the present invention.

FIG. 10 shows schematically a device 130 according to an alternative aspect of the invention. The device 130 may be configured from a network arrangement or similar arrangement of filaments 132 of a shape-memory alloy. A non-limiting example of a suitable shape-memory alloy is nitinol. The device is designed with an original relatively rigid configuration such that the radius is of suitable dimensions for optimal fit of a biological structure/s to be treated. Before use, the device may be cooled to a temperature below the critical temperature of nitinol. At such a temperature, the alloy is flexible and can be bent easily into any suitable shape for easy insertion of the biological and/or non-biological structures into the device. When the device warms up to body temperature, the nitinol is heated to its critical temperature and transforms into its original rigid arrangement. As such, using a change in temperature, the device may be configured for reversible radial enlargement and reversible radial contraction. The device 130 may be a tubular open ended device. The device 130 may include an elongated structure 134, which may include a first end 136 with a first opening 138 and a second end 140 with a second opening 142. The device 130 may be a hollow elongated structure with a cavity 144, which may be substantially hollow extending longitudinally between the first opening 138 and the second opening 142. The device 130 may include a joining line 146. The device 130 differs from a device constructed of a tubular braid in the way the device is contracted and expanded. The device 130 may feature all other suitable components as described hereinabove for tubular braid devices and may be adapted for all suitable uses described hereinabove for a tubular braid device. In one non-limiting example, a tubular braid device may be constructed from a shape memory-alloy and the resulting device may use both or either methods to facilitate reversible dimensions of the device and optimal accommodation of inserted structures.

Figure 11A:
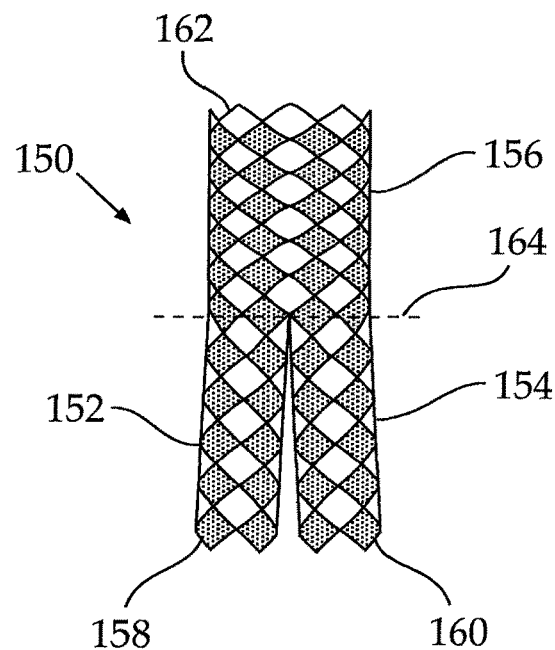
FIGS. 11a and 11b show schematic views of a multi-tubular device according to an aspect of the present invention.
Figure 11B:
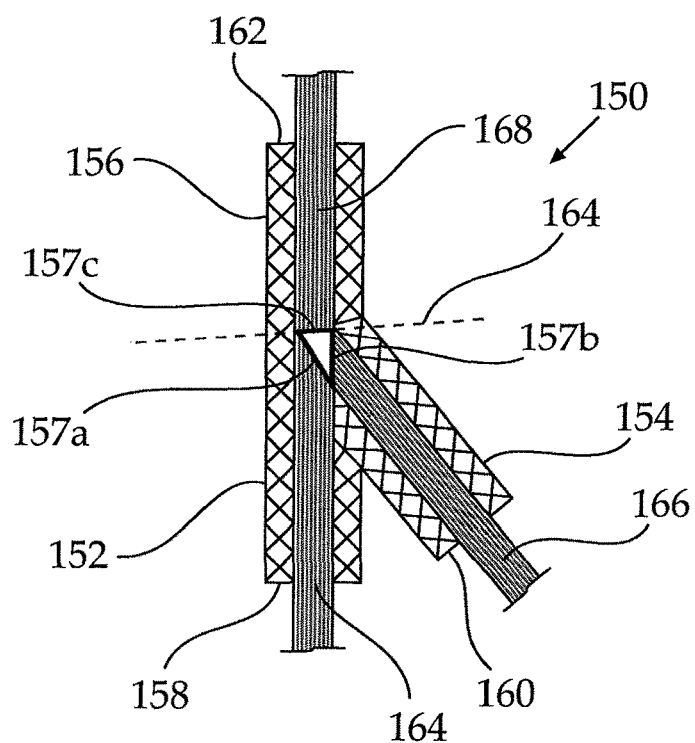

The present invention may provide an interconnected multi-tubular device. A multi-tubular device may include N interconnected tubular members, wherein N≥3, such as a multi-tubular device with at least three interconnected tubular members. Such a device may facilitate the joining of more than two structures. FIG. 11*a* shows schematically a multi-tubular device 150 according to an aspect of the invention. The device 150 shown in the figures includes three tubular members 152, 154 and 156. Each tubular member 152, 154 and 156 may be of the same dimensions or may have different dimensions. Each of the tubular members 152, 154 and 156 are similar to the device 10 described herein and shown in FIGS. 1, 2, 3a-3d, 4a and 4b. In order to avoid repetition, similar components, methods and properties relating to and as used in device 10 will not be described here. Each of the tubular members 152, 154, 156 may be constructed as a tubular braid or any suitable construction, which confers the properties of reversible radial contraction and expansion. A difference between device 10 and the tubular members 152, 154 and 156 is that each member 152, 154 and 156 is for accommodating only one structure within. The multi-tubular device 150 may include a plurality of openings 158, 160, 162, such as N openings corresponding to the openings at the distal ends of the N interconnected tubular members. As such, each member 152, 154 and 156 may provide the multi-tubular device with one open exposed end 158, 160 and 162 at an extremity of the multi-tubular device respectively forming the openings or extremities of the multi-tubular device. Each of the interconnected tubular members 152, 154, 156 include a second proximal end 157a, 157b, 157c as shown in FIG. 11b. The proximal ends of the interconnected tubular members are connected to each other such that the structures inserted through the distal openings of the tubular members into the cavities of the tubular members can contact and connect to each other at an internal point of the device adjacent to the joined proximal ends of the N interconnected tubular members. In the three tube device shown in FIG. 11b the proximal end 157a, 157b, 157c of one elongated member of the at least three interconnected members is connected to the proximal ends 157a, 157b, 157c of each of the elongated members of the at least three interconnected members to interconnect the elongated tubes and form a multi-tubular device. Structures 164, 166, 168, such as biological structures and/or non-biological structures inserted through the distal openings 158, 160, 162 of the multi-tubular device into the cavities of the elongated members 152, 154, 156 can contact and connect to each other at an internal point 164 of the multi-tubular device adjacent to the joined proximal ends 157a, 157b, 157c of the at least three interconnected tubular members 152, 154 and 156.

FIG. 11b shows schematically a first structure 164 may be inserted through the distal opening 158 into the cavity of tubular member 152 until a stop element. A second structure 166 may be inserted through the distal opening 160 into the cavity of tubular member 154 until a stop element. A third structure 168 may be inserted through the distal opening 162 into the cavity of tubular member 156 until a stop element. Each member 152, 154 and 156 may include uni-directional movement prevention means disposed in only one direction to promote insertion of only one biological or non-biological structure into the cavity of the tubular member to the joining line. The joining line 164 will not be substantially midway along each tubular member, but the joining line will be a line or an area at or adjacent to the point where the tubular members 152, 154, 156 meet. The multi-tubular device is configured so that the non-exposed proximal ends 157a, 157b, 157c of the tubular members 152, 154 and 156, which are positioned in the interior of the device and not at the extremities of the device 150 are joined and connected in a suitable way, such as but not limited to a T or Y configuration to provide a joined device 150 with three separate cavities, wherein inserted structures in the tubular members 152, 154, 156 can contact each other in a suitable way. The connection of the tubular members may be seamless. The inserted structures 164, 166 and 168 may be cut tissues, which are inserted into the multi-tubular device 150 in order that they can be joined. In the case of three biological structures, such as blood tissues, the blood tissues may be cut with angled cuts in order that the three structures can join and allow blood flow within and between the three structures. The device 150 may include more than three tubular members.

Figure 12:
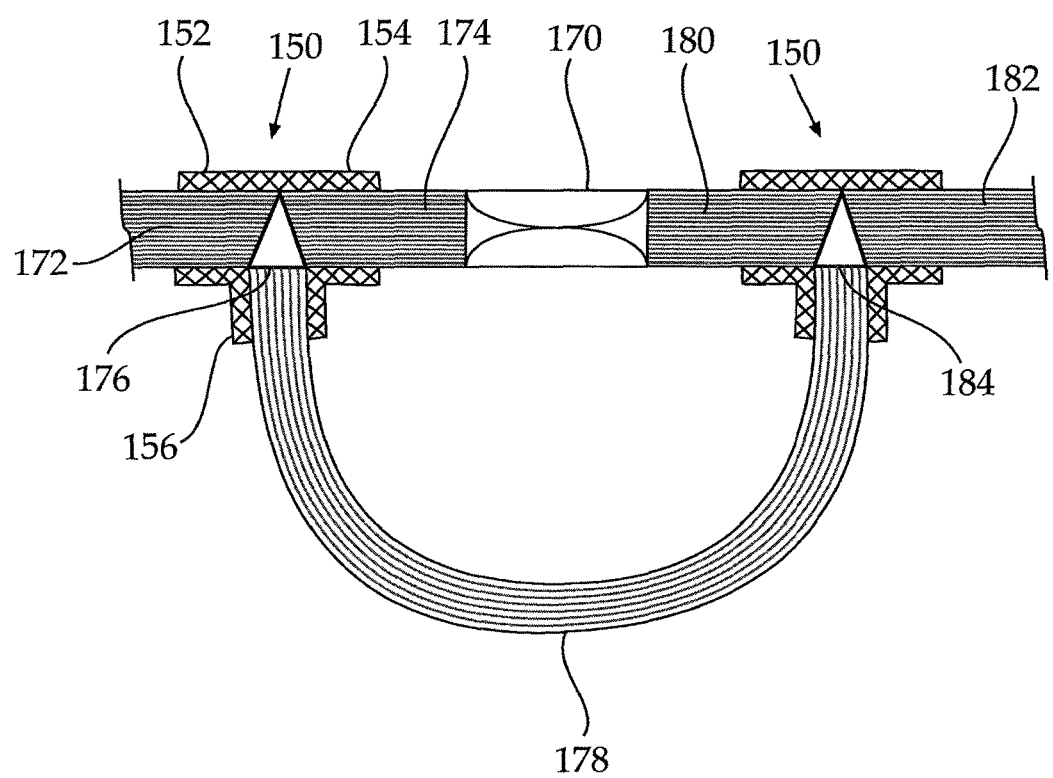
FIG. 12 shows a schematic view of a multi-tubular device connecting vessels in a bypass procedure according to an aspect of the present invention.

In one aspect, the multi-tubular device 150 of the present invention may be used in a bypass procedure for promoting optimal blood flow in a blocked blood vessel, such as a blocked artery. FIG. 12 shows schematically the multi-tubular device 150 of the present invention for use in bypassing according to one aspect of the invention. A biological structure, such as an artery with a blockage 170 is cross-sectionally cut before the blockage 170. The biological structure may be cut using an angled cut. The cut results in two parts, such as two cut ends of the biological structure 172, 174 before the blockage. A first biological structure cut end 172 may be inserted into one tubular member 152 of a multi-tubular member device 150, until a stop element. The second biological structure cut end 174 may be inserted into a second tubular member 154 of the device 150 until a stop element. One end 176 of a biological structure 178 for bypassing the blockage 170, such as a blood vessel from a suitable source, may be inserted into the cavity of the third tubular member 156 of the device 150 until a stop element. When inserted correctly into the multi-tubular device, the inserted ends of the two parts of the cut biological structure 172 and 174 and the inserted end of the bypassing biological structure 178 contact each other. Any pushing force on the device 150 may be removed and the multi-tubular device 150 may tighten around the biological structures accommodated in the device 150. A second multi-tubular device 150 may be employed in a similar way to accommodate the parts, such as the two cut ends of the biological structure 180, 182 which result from cutting of the artery after the blockage 170 and the second end 184 of the bypassing biological structure 178.

In an alternative aspect, the present invention may provide a device which is a device for wrapping around a structure. The device may not be shaped in a formed tubular construction, but may be configured as a flat braid or a flat net which may be wrapped around at least one biological structure and/or non-biological structure. Alternatively, the device may be made as a tubular braid, or net and the tube may be cut longitudinally. A user may apply the device, by wrapping the braid or net around the biological structure/s and forming a fixed tubular construction by attaching the relevant sides of the braid or net. Any suitable attachment components may be employed for attaching the relevant sides of the braid or net, wherein the attachment means facilitate a device with the properties of reversible radial enlargement and contraction. Such a device may be used in end to end connection and may also be used for non-end to end connection, such as but not limited to repair of a hole, a rip, a gash, a cut, a rupture or any damaged tissue, which is not severed.

In one aspect, the connector device of the present invention is relatively facile for use by a user. A user may be a doctor, a surgeon, a nurse, a medical technician, a veterinarian or any suitable medical professional or individual. The device may be used by more than one user. In one non-limiting example one medical professional may insert a biological structure into one opening of a device, whilst a second medical professional inserts a second structure into the second opening of the device or into an opening of a second part of a multi-part device. The device may be used to join a biological tissue to another biological tissue, or to join two parts of a biological tissue together or to join a biological tissue to a non-biological structure. The biological tissues may have been cut or damaged or may be in an unconnected state for any reason. The device may be used to join biological tissues that have been severed with any type of cut, such as but not limited to a cross-sectional cut, a straight cut, an angled cut and a combination thereof. The biological tissue/s to be joined may be located internally in the body of a patient. In one aspect, the device of the present invention may be configured to be used externally to connect severed or injured biological structures found externally, such as but not limited to fingers and toes. The device may be employed in this way on for example a severed finger for joining the parts of the finger or as an initial pretreatment before connection of the finger using other means. The connector device may be packaged in sterile packaging, which may be opened before use. The device may be inserted manually or may be inserted via suitable insertion means, which may be employed in for example keyhole surgery.

A user may perform any procedure necessary prior to, during and after use of the device of the present invention. In one non-limiting example, wherein a blood vessel has been cut, a clamp or a plurality of clamps or any equivalent may be applied at a suitable position of both parts of the severed blood vessel to temporarily stop or reduce blood flow. A user may select a device with dimensions suitable for optimally accommodating the structures to be inserted and joined. A user may push the ends of the device in order to expand the diameter of the device for more facile insertion of the structure to be accommodated. A user may then insert one severed end of the blood vessel or any suitable biological tissue through a first opening into the cavity of the connector device. The user may insert the tissue until at least one stop element prevents inserting the blood vessel deeper into the cavity of the device. The contacting surface of the device may include a layer of adhesive, which may temporarily adhere the tissue to a second tissue. A user may then, or simultaneously insert a second biological tissue or a second part of a biological tissue into the cavity of the elongated member through the second opposite opening of the tubular device of the present invention, until the tissue reaches the stop element and/or the first severed part of the blood vessel and the two parts of the blood vessel are contacted with each other. The user may stop pushing the ends of the device in order that the device automatically reverses to its original diameter or as close as possible to its original diameter and optimally fits around the inserted tissues. A user may pull the ends of the device, such that the diameter of the device is adjusted according to the diameter of the inserted biological tissue/s. Alternatively, or additionally, the blood vessel may move of its own accord away from the stop element towards the opening it was inserted through facilitating a pulling motion, which due to the configuration of the device results in a reduction of the radius of the cavity and secure holding of the tissue in the correct position. The tissue may also not be substantially displaced due to the unidirectional movement prevention means disposed on the contacting surface of the device.

Figure 13:
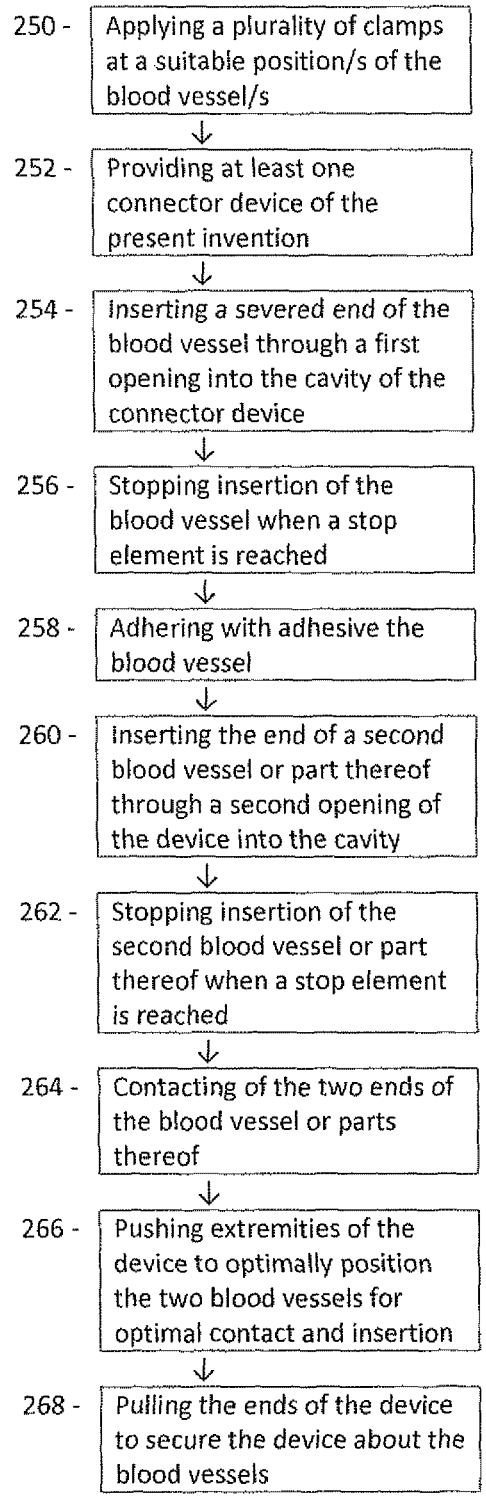
FIG. 13 shows a flow chart of a method of using the device according to one aspect of the present invention.

FIG. 13 shows a flow chart of a method of using the device according to one aspect of the invention. FIG. 13 shows a method of connecting end to end two parts of a blood vessel which has been severed. A plurality of clamps are applied at a suitable position of both parts of the severed blood vessel to temporarily stop or reduce blood flow and bleeding from the severed ends (250). A connector device of the present invention is provided (252), such as the device shown in FIG. 1. The connector device is chosen according to its extendable range of size in relation to the blood vessel to be joined. A user inserts one severed end of the blood vessel through a first opening of the tubular member of the device into the cavity of the connector device (254). The user may stop inserting the blood vessel when at least one stop element is reached, which prevents further deeper insertion into the cavity of the device (256). Surgical glue deposited in the coating of the internal surface of the device may contact the inserted blood vessel. The glue may be for adhering the blood vessel to a second part of the severed blood vessel (258). Adhering the blood vessel to a second part of the severed blood vessel may be done at a later stage after the second part of the severed blood vessel is inserted and both parts of the blood vessel are correctly positioned. A user may insert the end of the second part of the severed blood vessel into the cavity of the elongated member of the device through a second opposite opening of the tubular device of the present invention (260). The user may stop inserting the blood vessel when the blood vessel contacts at least one stop element and/or contacts the previously inserted first severed part of the blood vessel (262). The two parts of the blood vessel are contacted with each other (264). Surgical glue deposited in the coating of the internal surface of the device may contact the second part of the severed blood vessel. In some non-limiting examples, surgical glue is deposited in the coating such that it only contacts one extremity of the severed blood vessel. The two parts of the blood vessel may be adhered together with the surgical glue. The insertion of the second part of the severed blood vessel may be done simultaneously or after insertion of the first part of the severed blood vessel. In an optional step, the user may push the extremities of the device in order to reposition or optimally position the two parts of the severed blood vessel for optimal contact and connection (266). When the pushing force is removed, the diameter of the device will contract and return to its original dimensions or as near as possible. The user may pull the ends of the device, or the inserted parts of the blood vessel may move causing pulling of the device such that the diameter of the device is reduced and adjusted according to the diameter of the inserted biological tissue/s for secure holding of the tissue in the correct position (268). The steps of the method may be done in any suitable order.

In an alternative aspect when a multipart device is used, the user may insert a biological tissue or part thereof through a first opening into the cavity of the tubular member of one part of a multipart connector device. The user may position the tissue such that it is inserted in the first tubular member until a second proximal opening with attachment means. The correct positioning may be done visually. Alternatively, or additionally the device may include at least one stop element and the user may stop insertion when the movement of the biological tissue or part thereof is stopped by the at least one stop element. The user may insert a second biological tissue or second part thereof into the tubular member of a second separate part of a multipart connector device. The user may insert the second tissue or part of tissue into the second tubular member until it reaches the second proximal opening with attachment means and/or it contacts the at least one stop element. The user may then attach the first part of the multipart connector device to the second part of the multipart connector device by attaching corresponding attachment means of each part of the multipart connector device, which may be disposed about the at least one stop element of the first part and the second part of the multipart connector device. In one non-limiting example using female and male attachment components, the male part may be inserted into the female part for attachment of the two parts of the multipart device. A multipart device with more than two parts may also be used. Such a device may be suitable for connecting together more than two parts of a biological structure.

Figure 14:
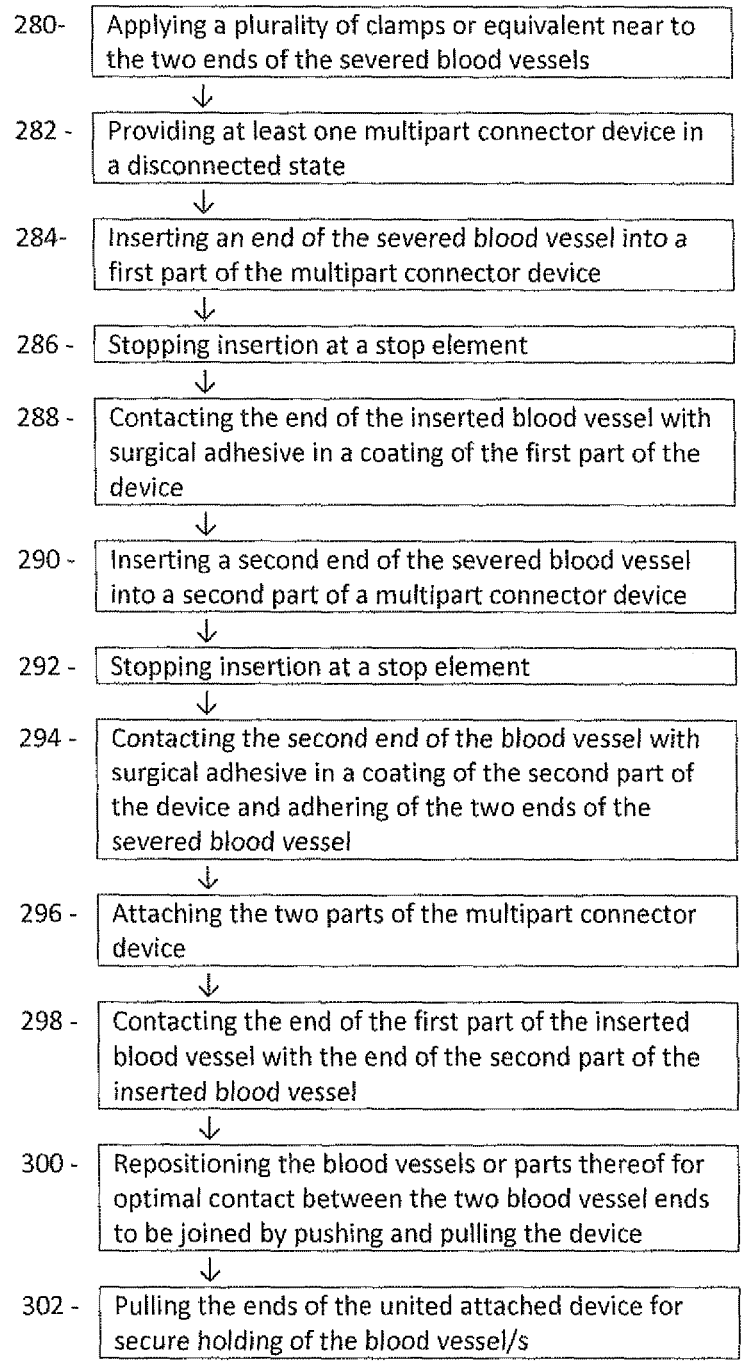
FIG. 14 shows a flow chart of a method of using a multipart device according to an aspect of the present invention.

FIG. 14 shows a flow chart of a method of using a multipart device according to an aspect of the invention. FIG. 14 shows a method of connecting two parts of a blood vessel which has been severed. A plurality of clamps or equivalent blood restriction elements are applied at a suitable position/s of both parts of the severed blood vessel to temporarily stop or reduce blood flow and bleeding from the severed ends (280). At least one multipart connector device of the present invention is provided (282). The multipart connector device is chosen according to its range of expandable size in relation to the blood vessel to be joined. A first part of the multipart device may be disconnected and separated from a second part of the multipart device. A user may insert one severed end of the blood vessel through a first opening at the distal end of a first part of the multipart device into the cavity of the tubular member of the first part of the multipart connector device towards the proximal end (284). The user may stop inserting the blood vessel when it reaches the proximal end and/or when at least one stop element is contacted (286). The at least one stop element may be a physical means and/or visual confirmation by a user that the blood vessel has reached the second opening of one part of the multipart device. The inner surface of the first part of the multipart device may include a surgical adhesive, which may be contacted with the inserted blood vessel. The glue may be for adhering, such as temporary adhering the inserted end of the blood vessel to a second end of the blood vessel inserted into a second part of the multipart device (288). Adhering may be done at a later stage after the second part of the severed blood vessel is inserted into the second part of the multipart device and both parts of the blood vessel are correctly positioned. In steps 290, 292 and 294, a user may repeat for a second part of the multipart device the steps described above for the first part of the multipart device (284, 286 and 288) relating to insertion of a second blood vessel or portion thereof, which is to be connected to the first blood vessel or portion thereof. In one non-limiting example the first part of a blood vessel is connected to a tube and the tube is inserted into the second part of the multipart device. The two parts of the multipart connector may be attached by attaching the corresponding attachment means at the proximal ends of the device parts adjacent to the severed ends of the blood vessel/s (296). After attachment of the two parts of the multipart device to form a connected unit, the two parts of the blood vessel may be contacted with each other (298). Optionally, the user may push and/or pull the extremities, such as the distal ends of the united connected multipart device in order to reposition or optimally position the two parts of the severed blood vessel for optimal contact and connection (300). When the pushing force is removed, the diameter of the device will contract and return to its original dimensions or as near as possible. The user may pull the distal ends of the connected multipart device, or the inserted parts of the blood vessel may move causing pulling of the device, such that the diameter of the device is reduced and adjusted according to the diameter/s of the inserted biological tissue/s for secure holding of the tissue/s in the correct position (302). Movement of the inserted tissue/s from the proximal end to the distal end of each part of the multipart device is prevented by at least one unidirectional movement prevention element. The order of the steps of the method is not meant to be limiting and any suitable order may be used.

Figure 15:
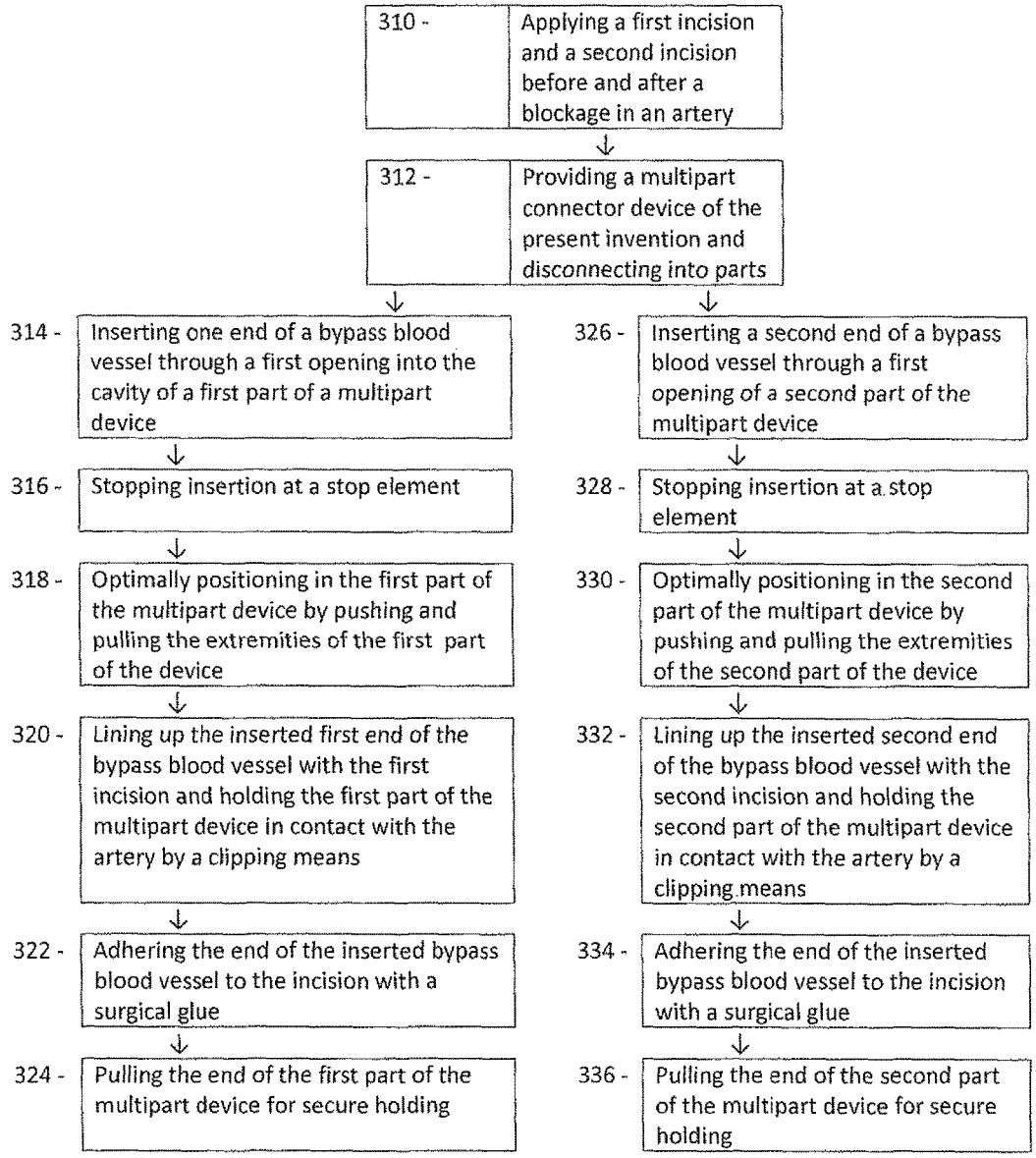
FIG. 15 shows a flow chart of a method of using the device in a bypass procedure according to an aspect of the present invention.

FIG. 15 shows a flow chart of a method of using a multipart device of the present invention in a bypass procedure according to an aspect of the invention. A user may make an incision at a suitable position before a blockage of a blood vessel, such as an artery and a second incision at a suitable position after the blockage (310). It is envisioned that all acceptable techniques and procedures, preparations and parts of the protocol used in typical bypass procedures will be included in a method herein. A difference is the use of the device of the present invention to connect the bypass blood vessel. A multipart connector device of the present invention is provided and the two parts of the device may be disconnected from each other (312). A first part of the multipart connector device may include a first tubular member and a second part of the multipart connector device may include a second tubular member. The multipart connector device is chosen according to the expandable and contractable range of size in relation to the size of the bypass blood vessel to be joined. A user inserts one end of an unblocked blood vessel from any suitable source, which is to be used as the bypass blood vessel through a first opening of a first part of the multipart device into the cavity of the device (314). The user stops inserting the bypass blood vessel when the proximal opening is reached and/or at least one stop element (316). The user may push and/or pull the extremities of the first part of the multipart device in order to reposition or optimally position the first end of the bypass blood vessel for optimal connection (318). The first part of the multipart device with the inserted first end of the bypass blood vessel is lined up against the incision in the artery before the blockage and a holding means which is positioned about the artery, clips or clamps the first part of the multipart device against the incision in the artery (320). The holding means may attach to an attachment means of the first part of the multipart device. The correct positioning facilitates flow of blood from the artery via the incision into the bypass blood vessel through the end of the bypass blood vessel accommodated in the first part of the multipart device. The device may include a surgical adhesive in the coating of the device which may facilitate adhering the blood vessel about the incision in the artery (322). The adhering may be done at any suitable stage of the process. The user may remove any pushing force and/or pull the ends of the first part of the multipart device, such that the diameter of the device is reduced and adjusted according to the diameter/s of the inserted bypass blood vessel for secure holding of the tissue in the correct position (324). In steps 326, 328, 330, 332, 334 and 336, a user may repeat steps 314-324 with the second part of the multipart connector device, inserting a second extremity of the bypass blood vessel into a second part of the multipart device of the present invention to connect the second extremity of the bypass blood vessel with the second incision after the blockage in the blocked artery. This method facilitates bypassing of the blockage in the blocked artery by connection of the bypass blood vessel to the blocked artery before and after the blockage with a plurality of parts of the multipart device of the present invention. The order of the steps of the method is not meant to be limiting and may be in any suitable order.

Figure 16:
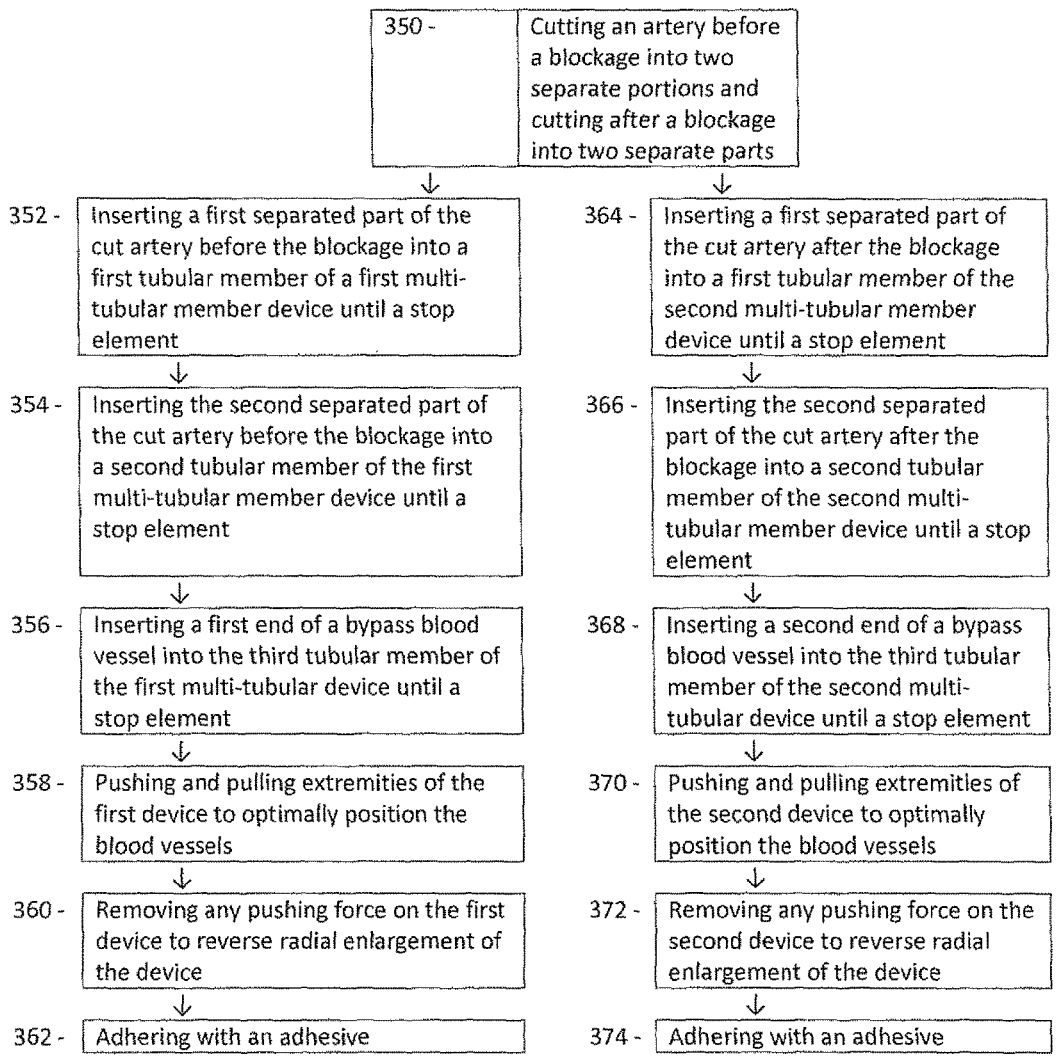
FIG. 16 shows a flow chart of a method of using a multi-tubular device in a bypass procedure according to an aspect of the present invention.

FIG. 16 shows a flow chart of a method of using a plurality of multi-tubular devices of the present invention in a bypass procedure according to an aspect of the invention. A user may cut a blocked blood vessel, such as for example an artery at a suitable position on a first side of a blockage before the blockage of an artery and a user may cut a blocked blood vessel, such as an artery at a suitable position on a second side of the blockage after the blockage (350). The cut before the blockage results in two separate portions of the artery before the blockage, such as a first cut end and a second cut end and the cut after the blockage results in two separate portions of the blocked artery after the blockage, such as a third cut end and a fourth cut end. It is envisioned that all acceptable techniques and procedures, preparations and parts of the protocol used in typical bypass procedures will be included in a method herein. A difference is the use of the multi-tubular device of the present invention to connect the blood vessels. A first portion of the cut artery before the blockage, such as the first cut end is inserted through a first opening into a first member of the multi-tubular device until a stop element is reached (352). The second portion of the cut artery before the blockage, such as the second cut end is inserted through a second opening into a second member of the multi-tubular device until a stop element is reached (354). A user inserts one end, a first end of an unblocked blood vessel from any suitable source, which is to be used as the bypass blood vessel through a third opening into the third tubular member of the multi-tubular device until a stop element is reached (356). The user may push and/or pull the extremities of the tubular members of the device in order to reposition or optimally position the blood vessels (358). Any pushing force on the device may be removed, such that the radius of the device contracts and the device optimally holds the inserted structures (360). The internal surface of the multi-tubular device may include an adhesive to aid in joining the cut blood vessels (362). The adhering may be done at any suitable stage of the process. Pulling the ends of the device by for example movement of the inserted blood vessels may result in radial contraction and further tightening of the device about the inserted structures. A user may repeat steps 352-362 with a second multi-tubular device (steps 364-374) to join the two portions of the blocked artery cut after the blockage and the second end of the bypass blood vessel. This method facilitates bypassing of the blockage in the blocked artery by connection of the bypass blood vessel to the blocked artery with a plurality of multi-tubular devices of the present invention. The order of the steps of the method is not meant to be limiting and may be in any suitable order.

The device of the present invention may remain connected to the biological tissue/s until the tissues join or rejoin or are healed. The device may be removed after the tissues have joined. In some aspects, the device may remain in the body. In some aspects, the device may degrade after the biological tissue/s have joined.

A user may treat the biological tissue prior to using the connector device of the present invention. In one aspect, the device may include at least one composition, which may treat the tissue.

A user may apply more than one connector device of the present invention according to need. The more than one connector devices may be applied to different parts of the same biological tissue or to different biological tissues. Application of the device of the present invention may be one step or any suitable number of steps of any suitable surgical or medical procedure.

The device of the present invention may be used instead of other methods of connecting biological tissues or in addition to such methods. In one aspect, the device of the present invention may be used in addition to suturing and may augment suturing. Such a combination of joining a biological tissue/s may be conducted using a multipart device of the present invention. Such a combination of methods is useful in a case where there is a need for reinforcement such as when there's a danger of stitches rupturing.

The device of the present invention may be produced by tubular braiding of a plurality of filaments of suitable material. The filaments may be sized according to the end use of the device. At least one unidirectional stop element may be applied to the filaments in a suitable direction according to the location in the device. The number of stop elements and their distribution are calculated according to the same rationale as the number of spikes described herein. The dimensions of the stop elements are calculated according to the same rationale as the dimensions of the spikes described herein. The material of the device, such as the filaments may include the stop elements or may be processed in a suitable way to provide at least one stop element in the material. The material may be precoated with adhesive or adhesive may be applied at a later stage. The material may be coated with any suitable coating. The manufacture may be done manually or mass produced in a production line by suitable machinery. The ends of the device may be given a relatively smooth finish by any suitable procedure such as tucking in or folding or gluing or stitching the ends of the braid so that the individual filaments or strips do not protrude or stick out in a way that can be detrimental to a biological structure.

Figure 17:
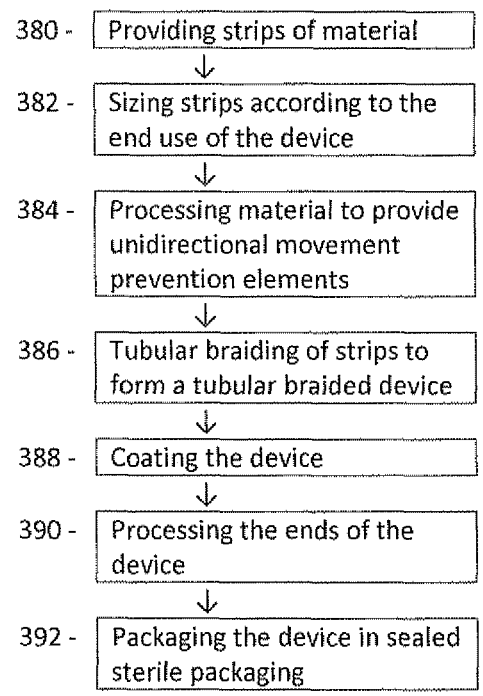
FIG. 17 shows a flow chart of a method of production of the device according to one aspect of the present invention.

FIG. 17 shows a flow chart of a method of making a device according to an aspect of the invention. A plurality of lengths of filaments or strips are provided, the number depending on the shape and size of the biological tissue to be joined and the intended porosity of the device (380). The filaments are sized according to the end use of the device (382). The material from which the filaments are made is processed to include unidirectional movement prevention elements (384). The unidirectional movement prevention elements are applied so that the first section featuring the first half of the device will include in its interior movement prevention elements promoting movement in only one direction and the second section featuring the second half of the device will include in its interior movement prevention elements promoting movement in only the opposing direction from the first section. The device is configured by tubularly braiding the lengths of filaments (386). Step 384 may be implemented after step 386 to ensure the unidirectional movement prevention elements are substantially parallel to the tubular braided device. At least one coating, such as but not limited to a glue, may be applied to the device (388). The material of the filaments may be precoated at any suitable stage. The ends of the device may be processed in order that the individual filaments do not dangerously protrude (390). The device may be packaged in a suitable sterile packaging, which may be sealed (392). The order of the steps of the method is not meant to be limiting and may be in any suitable order.

Reference is made to the following examples, which together with the above descriptions illustrate the invention in a non-limiting fashion.

Example 1—Preparation of a Tubular Braid

Eight strips of silicone were provided. Each strip had the following dimensions: Length=about 16 mm; width=about 1.8 mm; and thickness=about 1.0 mm. Scissors were used to cut out spikes on each strip, wherein the strip formed the base of each spike. The spikes made in the first half of the strip were formed so that the spikes all bent in one direction, towards the midline of the final tubular braid. The spikes in a second half of the strip were made so that the spikes bent in an opposite direction to the first spikes. Adhesive was applied to parts of the surface of the strips. The layer of adhesive applied was sufficiently thin so that it did not affect the function of the spikes or the function of the device. The strips were braided using pairs of strips to form a tubular braid. The hollow tubular braid had two openings, one at each end of the elongated member. The cavity had an inner diameter of about 5 mm.

Example 2—Testing Tubular Braid for Reversible Contraction and Expansion

The tubular braid made in Example 1 was checked for properties of reversible contraction and expansion. When the ends of the braid were pushed inwards towards the center of the elongated member, the diameter of the cavity increased to a maximum of about 5.5 mm. When the two ends of the braid were pulled in an opposite direction, the diameter of the cavity was reduced to a minimum of up to about 3.5 mm. The diameter of the device was increased and decreased in this way several times. Once the pulling and pushing was stopped, the device returned to its original state with original diameter of about 5 mm. The device was found to exhibit reversible radial contraction and expansion.

Example 3—Evaluation of the Device for Holding Two Structures

A silicone tube of length, of about 16 mm; outer diameter of about 4 mm; and thickness of about 1.0 mm was cut vertically into two, resulting in two tubes of smaller length. The tubular braid of Example 1 was pushed from both ends inwards to increase the radius of the cavity and then one of the tubes was inserted into the hollow braid through one of the ends of the tubular braid. The tube was inserted until it reached opposing spikes which stopped any further insertion. The second tube was then inserted into the tubular braid through the second end of the braid. The second tube was inserted until it contacted the immersed end of the first inserted tube. The pushing force was removed and the radial expansion was reversed resulting in the radius returning to the original resting state radius size. This contraction facilitated the braid tightening around the tubes. Any movement of either of the tubes in a direction opposite from the direction the tube/s were inserted resulted in a pulling of the braid which caused further tightening around the tubes.

Example 4—Tubular Braid Hose Device

A commercially available tubular braid used to protect hoses was purchased from Transtechnica Fluid Control & Sealing 2001 Ltd., Holon, Israel. The tubular braid made from metal wires was very flexible and could be easily bent. When the ends of the braid were pushed inwards towards the midline of the braid, the radius of the cavity enlarged. When the ends of the braid were pulled away from the midline of the braid, the radius was reduced. However, when the pulling or pushing forces were removed, the braid did not return by itself to its original state. The braid was configured for bending and folding and with flexibility properties, which prevented the automatic reversibility of the radial contraction and expansion on removal of the pushing and pulling forces inherent to the device of the present invention. As such, the hose protection braided device was found to be incompatible for the purposes of the present invention.

Example 5—Construction of a Silicone Braid with Spikes Positioned Parallel to Each Strip Eight strips of silicone were provided. Each strip had the following dimensions: Length=about 16 mm; width=about 1.8 mm; and thickness=about 1.0 mm. Scissors were used to cut out spikes on each strip, wherein the strip formed the base of each spike. The spikes were positioned spaced apart and in a line parallel to each strip. The spikes made in the first half of the strip were formed so that the spikes all bent in one direction, towards the midline of the strip. The spikes in a second half of the strip were made so that the spikes bent in an opposite direction to the first spikes. Adhesive was applied to parts of the surface of the strips. The layer of adhesive applied was sufficiently thin so that it did not affect the function of the spikes or the function of the device. The strips were braided using pairs of strips to form a tubular braid. The hollow tubular braid had two openings, one at each end of the elongated member. The cavity had a diameter of about 5 mm. The spikes of the formed device were found to be positioned at an angle to the formed device and as such would not be parallel to any structure inserted in the device. Such an angular spacing of the spikes was not found to facilitate optimal unidirectional movement prevention.

Example 6—Construction of a Silicone Braid with Spikes Positioned Parallel to the End Device Eight strips of silicone were provided. Each strip had the following dimensions: Length=about 16 mm; width=about 1.8 mm; and thickness=about 1.0 mm. Scissors were used to cut out spikes on each strip, wherein the strip formed the base of each spike. The spikes were positioned at an angle along each strip. The angle was determined in order that the spikes would be positioned in the end device parallel to an inserted structure, for optimal functioning as unidirectional movement prevention means. The spikes made in the first half of the strip were formed so that the spikes all bent in one direction, towards the midline of the final tubular braid. The spikes in a second half of the strip were made so that the spikes bent in an opposite direction to the first spikes. Adhesive was applied to parts of the surface of the strips. The layer of adhesive applied was sufficiently thin so that it did not affect the function of the spikes or the function of the device. The strips were braided using pairs of strips to form a tubular braid. The hollow tubular braid had two openings, one at each end of the elongated member. The cavity had an inner diameter of about 5 mm. The spikes were shown to be positioned in the same line as the formed tubular braid device in order to be parallel to a structure inserted in the device and facilitate unidirectional movement prevention.

Example 7—Construction of a Nitinol Braided Connector Device

Eight strips of nitinol were provided. Each strip had the following dimensions: Length=about 5.7 mm; width=about 1.8 mm; and thickness=about 0.1 mm. The strips were braided using pairs of strips to form a tubular braid. The hollow tubular braid had two openings, one at each end of the elongated member. The length of the elongated member was about 4 mm. The cavity had a diameter of about 6 mm.

Example 8—Evaluation of a Nitinol Connector Device for Joining Two Parts of a Severed Blood Vessel The connector device of Example 7 was evaluated for joining end to end two parts of a severed blood vessel. An Advanta™ SST graft used clinically in the place of veins was purchased from Atrium. The diameter of the graft was approximately 6 mm. The graft was cut vertically into two parts to simulate a severed vein, which required end to end connection. The extremities of the Nitinol connector device were pushed towards the center of the device, facilitating radial expansion of the device and the severed end of a first part of the graft was inserted through a distal opening of the device into the internal cavity of the connector device. Insertion was stopped at a joining line, which was defined as the middle line of the device. The severed end of the second part of the graft was inserted through a second proximal opening of the device into the internal cavity of the device. Insertion was stopped when the severed end of the second part of the graft contacted the severed end of the first part of the graft. The pushing forces were removed and the device held firmly the two parts of the graft, maintaining optimal contact between the two severed ends of the graft.

One skilled in the art can appreciate from the foregoing description that the broad devices and techniques of the aspects of the present invention can be implemented in a variety of forms. Therefore, while the aspects of this invention have been described in connection with particular examples thereof, the true scope of the aspects of the invention should not be so limited since other modifications will become apparent to the skilled practitioner upon a study of the specification, and following claims.

What is claimed is:

1. A device for connecting a biological structure with at least one other structure, the device comprising: a tubular member including:
   a longitudinal axis, a radial axis at least substantially perpendicular to the longitudinal axis, an oppositely disposed first distal end and a second proximal end, the first end including a first opening, the second end including a second opening;
   a plurality of braided lengths extending from the first end to the second end, the plurality of braided lengths configured for: 1) reversible radial enlargement of the tubular member in response to a pushing force being applied to at least one of the first end or the second end of the tubular member, the pushing force acting in the direction of the longitudinal axis, and 2) reversible radial contraction of the tubular member in response to a pulling force being applied to at least one of the first end or the second end of the tubular member, the pulling force acting in the direction of the longitudinal axis;
   an inner surface and a lumen defining a cavity for accommodating a biological structure, the cavity accessible through the first opening; and
   at least one unidirectional movement prevention element extending into the cavity, for promoting unidirectional movement of a biological structure in the direction of the longitudinal axis inwards into the cavity from the first opening, and opposing unidirectional movement of a biological structure received in the cavity in an opposite direction of the longitudinal axis out of the cavity towards the first opening.

2. The device of claim 1, wherein the cavity includes a first section accessible through the first opening, the first section for accommodating a biological structure inserted through the first opening and a second section for accommodating another structure inserted through the second opening.

3. The device of claim 2, wherein the first section contacts the second section at a joining line, the joining line including at least one stop element for preventing displacement of an inserted structure beyond the stop element deeper into the cavity.

4. The device of claim 3, wherein the first section comprises at least one movement prevention element for promoting unidirectional movement in a direction through the first opening and towards the joining line and opposing unidirectional displacement of a biological structure away from the joining line towards the first opening, and wherein the second section comprises at least one movement prevention element for promoting unidirectional movement in a direction through the second opening towards the joining line and opposing unidirectional displacement away from the joining line and towards the second opening.

5. The device of claim 4, wherein the at least one movement prevention element of both of the first section and the second section includes a spike.

6. The device of claim 5, wherein the each said spike is positioned substantially parallel to the longitudinal axis of the tubular member.

7. The device of claim 1, wherein the plurality of interwoven lengths are configured as a tubular braid and wherein the ends of the interwoven lengths are folded into the braid.

8. The device of claim 1, comprising a plurality of the tubular members, each tubular member including an attachment means at the proximal end thereof, wherein the attachment means of a first one of the tubular members corresponds with the attachment means of a second one of the tubular members for attachment of the proximal end of the first tubular member to the proximal end of the second tubular member to form a multi-part device for end to end attachment of a biological structure accommodated in the cavity of the first tubular member and another structure accommodated in the second tubular member.

9. The device of claim 8, wherein the inner surface of the plurality of the tubular members comprises at least one unidirectional movement prevention element for preventing displacement of the inserted biological structure away from the proximal end of the tubular member towards the distal end of the tubular member.

10. The device of claim 9, wherein the at least one unidirectional movement prevention element includes at least one spike.

11. The device of claim 10, wherein the at least one spike is positioned substantially parallel to the longitudinal axis of the tubular member.

12. The device of claim 8, wherein the plurality of braided lengths are configured as a tubular braid and wherein the ends of the braided lengths are folded into the braid.

13. The device of claim 1 comprising N≥3 interconnected tubular members, the device having N openings corresponding to the openings at the distal ends of the N interconnected tubular members, wherein the proximal ends of the N interconnected tubular members are connected to each other such that at least one of biological structures or other other structures inserted through the distal openings of the tubular members into the cavities of the tubular members can contact and connect to each other at an internal point of the device adjacent to the joined proximal ends of the N interconnected tubular members.

14. The device of claim 13, wherein the internal point includes at least one stop element for preventing displacement of the at least one biological structure or other structure beyond the stop element.

15. The device of claim 13, wherein the inner surface of at least one of the tubular members includes at least one unidirectional movement prevention element for preventing displacement of the inserted biological structure away from the proximal end of that tubular member towards the distal end of that tubular member.

16. The device of claim 13, wherein the plurality of braided lengths are configured as a tubular braid and wherein the ends of the braided lengths are folded into the braid.

17. The device of claim 1, wherein the shape of the device conforms to the shape of the biological structure.

18. The device of claim 1, wherein the tubular member is constructed from at least one material selected from the group consisting of metal, plastic, nitinol, alloys of titanium and nickel, stainless steel, platinum, gold, silver, copper, zinc, silicone, ceramic, polytetrafluoroethylene (PTFE), polyethylene, urethane, nylon, polyester, polypropylene, fabric, gut and tissue graft and combinations thereof.

19. The device of claim 1, wherein an internal surface of the tubular member is coated with at least one layer of coating.

20. The device of claim 19, wherein each at least one layer of coating includes at least one material selected from the group consisting of an adhesive, a glue, a surgical glue, a fibrin sealant, a collagen based compound, a glutaraldehyde glue, a hydrogel, a dye, an antibiotic, an antibacterial, an anti-clotting substance, a vitamin, a promoter of healing, a therapeutic agent, an anticlotting substance, a clotting substance, an antioxidant, an anti-inflammatory agent, an anesthetic agent, an anti-coagulant, an anti-restenosis agent, a thrombosis agent, an immunosuppressant agent and a movement retardation composition.

21. The device of claim 1, the tubular member comprising contractible dimensions for facilitating tightening around a biological structure received in the cavity of the tubular member.

* * * * *